(12) United States Patent
Lemire et al.

(10) Patent No.: US 10,980,778 B2
(45) Date of Patent: Apr. 20, 2021

(54) METHODS FOR TREATING MULTIPLE OSTEOCHONDROMA (MO)

(71) Applicant: Clementia Pharmaceuticals Inc., Montreal (CA)

(72) Inventors: Isabelle Lemire, Montreal (CA); Michael Harvey, Kirkland (CA); Donna Roy Grogan, Boston, MA (US); Clarissa Desjardins, Westmount (CA)

(73) Assignee: Clementia Pharmaceuticals Inc., Montreal (CA)

( * ) Notice: Subject to any disclaimer, the term of this patent is extended or adjusted under 35 U.S.C. 154(b) by 130 days.

(21) Appl. No.: 16/349,847

(22) PCT Filed: Nov. 16, 2017

(86) PCT No.: PCT/CA2017/051368
§ 371 (c)(1),
(2) Date: May 14, 2019

(87) PCT Pub. No.: WO2018/090137
PCT Pub. Date: May 24, 2018

(65) Prior Publication Data
US 2019/0275005 A1 Sep. 12, 2019

Related U.S. Application Data

(60) Provisional application No. 62/423,019, filed on Nov. 16, 2016.

(51) Int. Cl.
*A61K 31/415* (2006.01)
*A61P 19/00* (2006.01)
*A61P 35/00* (2006.01)
*A61K 9/00* (2006.01)

(52) U.S. Cl.
CPC .......... *A61K 31/415* (2013.01); *A61K 9/0053* (2013.01); *A61P 19/00* (2018.01); *A61P 35/00* (2018.01)

(58) Field of Classification Search
CPC .................................................. A61K 31/415
See application file for complete search history.

(56) References Cited

U.S. PATENT DOCUMENTS

| | | | |
|---|---|---|---|
| 5,624,957 A | 4/1997 | Swann et al. | |
| 5,760,084 A | 6/1998 | Swann et al. | |
| 5,824,685 A | 10/1998 | Campochiaro et al. | |
| 6,187,950 B1 | 2/2001 | Song et al. | |
| 6,204,288 B1 | 3/2001 | Pershadsingh et al. | |
| 6,313,168 B1 | 11/2001 | Pacifici et al. | |
| 6,777,418 B2 | 8/2004 | Lapierre et al. | |
| 6,838,472 B2 | 1/2005 | Klaus et al. | |
| 6,844,466 B2 | 1/2005 | Belloni et al. | |
| 7,345,931 B2 | 3/2008 | Partsch et al. | |
| 7,547,687 B2 | 6/2009 | Reading et al. | |
| 9,045,484 B2 | 6/2015 | Yu et al. | |
| 9,314,439 B2 | 4/2016 | Iwamoto et al. | |
| 9,492,431 B2 | 11/2016 | Kimura | |
| 9,750,721 B2 | 9/2017 | Kimura | |
| 9,789,074 B2 | 10/2017 | Iwamoto et al. | |
| 2002/0082265 A1 | 6/2002 | Lapierre et al. | |
| 2003/0113913 A1 | 6/2003 | Purton et al. | |
| 2003/0114482 A1 | 6/2003 | Pacifici et al. | |
| 2003/0125252 A1 | 7/2003 | Underhill et al. | |
| 2005/0271705 A1 | 12/2005 | Hughes et al. | |
| 2006/0210638 A1 | 9/2006 | Liversidge et al. | |
| 2009/0074789 A1 | 3/2009 | Sabbadini et al. | |
| 2009/0176862 A1 | 7/2009 | Chandraratna et al. | |
| 2009/0214493 A1 | 8/2009 | Pittenger et al. | |
| 2009/0281184 A1 | 11/2009 | Sawada et al. | |
| 2011/0076318 A1 | 3/2011 | Hughes et al. | |
| 2012/0077786 A1 | 3/2012 | Byron et al. | |
| 2012/0277156 A1 | 11/2012 | Gross et al. | |
| 2013/0189319 A1 | 7/2013 | Cook et al. | |
| 2014/0220154 A1 | 8/2014 | Regard et al. | |
| 2014/0303223 A1 | 10/2014 | Iwamoto et al. | |
| 2014/0363402 A1 | 12/2014 | Iwamoto et al. | |
| 2015/0290172 A1 | 10/2015 | Kimura | |
| 2016/0120843 A1 | 5/2016 | Kimura | |

(Continued)

FOREIGN PATENT DOCUMENTS

| | | |
|---|---|---|
| EP | 3000466 A1 | 3/2016 |
| JP | 2005-206544 A | 8/2005 |
| WO | WO-01/80894 A2 | 11/2001 |

(Continued)

OTHER PUBLICATIONS

Clinical Brief, Examining Quality of Life and Treatment Options for Fibrodysplasia Ossificans Progressiva and Multiple Osteochondromas, 2019, The American Journal of Managed Care, pp. 1-6 (Year: 2019).*
"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans. Progressiva (FOP)," U.S. National Library of Medicine, <https://clinicaltrials.gov/ct2/history/NCT02190747?V_12=View#StudyPageTop>, dated Aug. 25, 2015, retrieved on Dec. 17, 2019 (5 pages).
"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans Progressiva (FOP)," U.S. National Library of Medicine, <https://clinicaltrials.gov/ct2/history/NCT02190747?V_1=View#StudyPageTop>, dated Jul. 14, 2014, retrieved on Dec. 17, 2019 (5 pages).

(Continued)

*Primary Examiner* — Kortney L. Klinkel
*Assistant Examiner* — Tori Strong
(74) *Attorney, Agent, or Firm* — Clark & Elbing LLP

(57) ABSTRACT

The invention features methods for inhibiting the formation, reducing the size, and slowing the growth of an osteochondroma in a subject with multiple osteochondroma (MO) by administering to the subject palovarotene (also known as R667), or a pharmaceutically acceptable salt thereof. The methods described herein can also ameliorate complications associated with osteochondroma formation and growth in a subject with MO.

23 Claims, 4 Drawing Sheets

(56) References Cited

U.S. PATENT DOCUMENTS

2017/0065562 A1 3/2017 Kimura
2017/0182079 A1 6/2017 Levi et al.

FOREIGN PATENT DOCUMENTS

| WO | WO-02/28810 A2 | 4/2002 |
| --- | --- | --- |
| WO | WO-2005/115304 A2 | 12/2005 |
| WO | WO-2010/071583 A1 | 6/2010 |
| WO | WO-2010/088735 A1 | 8/2010 |
| WO | WO-2012/030919 A2 | 3/2012 |
| WO | WO-2012/125724 A1 | 9/2012 |
| WO | WO-2012/129562 A2 | 9/2012 |
| WO | WO-2014/138088 A1 | 9/2014 |
| WO | WO-2014/160203 A2 | 10/2014 |
| WO | WO-2016/054406 A1 | 4/2016 |
| WO | WO-2017/070194 A1 | 4/2017 |
| WO | WO-2017/210792 A1 | 12/2017 |

OTHER PUBLICATIONS

"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans Progressiva (FOP)," U.S. National Library of Medicine, <https://clinicaltrials.gov/ct2/history/NCT02190747?V_16=View#StudyPageTop>, dated Mar. 1, 2016, retrieved on Dec. 17, 2019 (5 pages).

"A Phase 2 Randomized, Double-Blind, Placebo-Controlled Efficacy and Safety Study of a RAR gamma-Specific Agonist (Palovarotene) in the Treatment of Preosseous Flare-ups in Subjects with Fibrodysplasia Ossificans Progressiva (FOP)," U.S. National Library of Medicine, <https://clinicaltrials.gov/ct2/history/NCT02190747?V_17=View#StudyPageTop>, dated Apr. 4, 2016, retrieved on Sep. 30, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, <https://clinicaltrials.gov/ct2/history/NCT02279095?V_14=View#StudyPageTop>, dated Feb. 10, 2017, retrieved on Dec. 17, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, <https://clinicaltrials.gov/ct2/history/NCT02279095?V_1=View#StudyPageTop>, dated Oct. 28, 2014, retrieved on Dec. 20, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, <https://clinicaltrials.gov/ct2/history/NCT02279095?V_7=View#StudyPageTop>, dated Jan. 7, 2016, retrieved on Dec. 17, 2019 (5 pages).

"A Phase 2, Open-Label Extension, Efficacy and Safety Study of a RAR gamma Specific Agonist (Palovarotene) in the Treatment of Preosseous Flare-ups in Subjects With Fibrodysplasia Ossificans Progressiva (FOP)," U.S. National Library of Medicine, <https://clinicaltrials.gov/ct2/history/NCT02279095?V_8=View#StudyPageTop>, dated Jun. 9, 2016, retrieved on Dec. 17, 2019 (5 pages).

"Palovarotene drug may prevent multiple muscloskeletal problems linked with FOP," News Medical Life Sciences, <https://www.news-medical.net/news/20160415/Palovarotene-drug-may-prevent-multiple-musculoskeletal-problems-linked-with-FOP.aspx>, dated Apr. 15, 2016 (3 pages).

Brennan et al., "Mast cell inhibition as a therapeutic approach in fibrodysplasia ossificans progressiva (FOP)," Bone. http://dx.doi.org/10.1016/j.bone.2017.08.023 (2017) (8 pages).

Cahill et al., "KIT Inhibition by Imatinib in Patients with Severe Refractory Asthma," available in PMC Nov. 18, 2017, published in final edited form as: N Engl J Med. 376(20):1911-20 (2017) (17 pages).

Chakkalakal et al., "Palovarotene Inhibits Heterotopic Ossification and Maintains Limb Mobility and Growth in Mice With the Human ACVR1(R206H) Fibrodysplasia Ossificans Progressiva (FOP) Mutation," J Bone Miner Res. 31(9):1666-75 (2016).

Ciavarella et al., "20 novel point mutations and one large deletion in EXT1 and EXT2 genes: report of diagnostic screening in a large Italian cohort of patients affected by hereditary multiple exostosis," Gene. 515(2):339-48 (2013) (10 pages).

Clement et al., "Use of imatinib in the prevention of heterotopic ossification," HSS J. 9(2):166-70 (2013).

Convente et al., "Depletion of Mast Cells and Macrophages Impairs Heterotopic Ossification in an Acvr1R206H Mouse Model of Fibrodysplasia Ossificans Progressiva," J Bone Miner Res. 33(2):269-82 (2018).

Cuellar et al., "Cell biology of osteochondromas: bone morphogenic protein signalling and heparan sulphates," Int Orthop. 37(8):1591-6 (2013).

Czajka et al., "What is the Proportion of Patients With Multiple Hereditary Exostoses Who Undergo Malignant Degeneration?" Clin Orthop Relat Res. 473(7):2355-61 (2015).

Danziger et al., "Automated site-directed drug design: a general algorithm for knowledge acquisition about hydrogen-bonding regions at protein surfaces," Proc R Soc Lond B Biol Sci. 236(1283):101-13 (1989).

Di Rocco et al., "Selective RAR gamma agonist blocks heterotopic ossification and promotes skeletal muscle repair," ASBMR Oct. 4, 2013, (Abstract only) (2 pages).

Di Rocco et al., "Selective retinoic acid receptor gamma agonists promote repair of injured skeletal muscle in mouse," Am J Pathol. 185(9):2495-504 (2015).

Duncan et al., "The link between heparan sulfate and hereditary bone disease: finding a function for the EXT family of putative tumor suppressor proteins," J Clin Invest. 108(4):511-6 (2001).

Einhorn et al., "Bone regeneration: new findings and potential clinical applications," J Am Acad Orthop Surg. 9(3):157-65 (2001).

English translation of Japanese Patent Application No. 2005-206544, dated Nov. 23, 2015 (14 pages).

English Translation of Notice of Defects in Patent for Israeli Patent Application No. 224973, dated Dec. 16, 2015 (2 pages).

English translation of Office Action for Chilean Patent Application No. 201300580, dated Dec. 27, 2017 (6 pages).

English Translation of Office Action for Eurasian Patent Applicaiton No. 201370051, dated Jun. 1, 2015 (4 pages).

Examination Report for Australian Patent Application No. 2015200760, dated Mar. 2, 2016 (4 pages).

Extended European Search Report for European Application No. 17870813.7, dated Nov. 11, 2020 (6 pages).

Extended European Search Report for European Patent Application No. 11822537.4, dated Feb. 7, 2014 (10 pages).

First Examination Report for New Zealand Patent Application No. 706089, dated Mar. 25, 2015 (3 pages).

Further Examination Report for New Zealand Patent Application No. 607547, dated Mar. 25, 2015 (2 pages).

Further Examination Report for New Zealand Patent Application No. 607547, dated Nov. 19, 2014 (2 pages).

Gannon et al., "Mast cell involvement in fibrodysplasia ossificans progressiva," Hum Pathol. 32(8):842-8 (2001).

Halevy et al., "Retinoic acid induces adult muscle cell differentiation mediated by the retinoic acid receptor-alpha." J Cell Physiol. 154(3):566-72 (1993).

Hesse, "Muscle and Bone: Combating the Evil Side of the Connection," J Bone Miner Res. 31(9):1647-51 (2016).

Hopkins, "Inhibitors of the bone morphogenetic protein (BMP) signaling pathway: a patent review (2008-2015)," Expert Opin Ther Pat. 26(10):1115-28 (2016) (15 pages).

(56) References Cited

OTHER PUBLICATIONS

International Search Report and Written Opinion for International Application No. PCT/CA2017/050701, dated Aug. 30, 2017 (16 pages).
International Search Report and Written Opinion for International Application No. PCT/CA2017/051368, dated Feb. 7, 2018 (11 pages).
International Search Report and Written Opinion for International Application No. PCT/CA2018/051595, dated Aug. 15, 2019 (11 pages).
International Search Report and Written Opinion for International Application No. PCT/CA2019/051803, dated Feb. 20, 2020 (10 pages).
International Search Report for International Application No. PCT/US2011/049905, dated May 1, 2012 (4 pages).
Inubushi et al., "Palovarotene Inhibits Osteochondroma Formation in a Mouse Model of Multiple Hereditary Exostoses," J Bone Miner Res. 33(4):658-66 (epub-2017) (9 pages).
Iwamoto et al., "Retinoic acid induces rapid mineralization and expression of mineralization-related genes in chondrocytes," Exp Cell Res. 207(2): 413-420 (1993).
Japanese Office Action with English translation for Japanese Patent Application No. 2013-527250, dated Jul. 30, 2015 (6 pages).
Jones et al., "TESRA (Treatment of Emphysema With a Selective Retinoid Agonist) Study Results," Am J Respir Crit Care Med. 183:A6418 (2011) (2 pages).
Juurikivi et al., "Inhibition of c-kit tyrosine kinase by imatinib mesylate induces apoptosis in mast cells in rheumatoid synovia: a potential approach to the treatment of arthritis," Ann Rheum Dis. 64(8):1126-31 (2005).
Kaplan et al., "Derailing heterotopic ossification and RARing to go," Nat Med. 17(4):420-421 (2011).
Kaplan et al., "Early clinical observations on the use of imatinib mesylate in FOP: A report of seven cases," Bone. 109:276-80 (2018).
Kennedy et al., "Retinoic acid enhances skeletal muscle progenitor formation and bypasses inhibition by bone morphogenetic protein 4 but not dominant negative beta-catenin," BMC Biol. 7:67 (2009). (21 pages).
Koyama et al., "Retinoid signaling is required for chondrocyte maturation and endochondral bone formation during limb skeletogenesis," Dev Biol. 208(2):375-91 (1999).
Krueger C et al., "Identification of Retinoic Acid in a High Content Screen for Agents that Overcome the Anti-Myogenic Effect of TGF-Beta-1," PLoS ONE 5(11): e15511 (2010) (11 pages).
Le May et al., Retinoid X Receptor Signalling in the Specification of Skeletal Muscle Lineage. *Skeletal Muscle—From Myogenesis to Clinical Relations*. Juliana Cseri, 49-72 (2012).
Matsumoto et al., "Conditional ablation of the heparan sulfate-synthesizing enzyme Ext1 leads to dysregulation of bone morphogenic protein signaling and severe skeletal defects," J Biol Chem. 285(25):19227-34 (2010).
Neuville et al., "Retinoic acid regulates arterial smooth muscle cell proliferation and phenotypic features in vivo and in vitro through an RAR alpha-dependent signaling pathway," Arterioscler Thromb Vasc Biol. 19:1430-6 (1999).
Office Action and English Comments for Mexican Patent Application No. MX/a/2013/002275, dated Jan. 12, 2018 (7 pages).
Office Action and English Comments for Mexican Patent Application No. MX/a/2013/002275, dated Jan. 12, 2016 (8 pages).
Office Action and English Comments for Thai Patent Application No. 1301001049, received Jul. 1, 2015 (5 pages).
Office Action and its English translation for Chinese Patent Application No. 201180052926.X, dated May 8, 2014 (19 pages).
Office Action for Canadian Patent Application No. 2809374, dated Dec. 1, 2017 (4 pages).
Office Action for U.S. Appl. No. 14/308,570, dated Jul. 31, 2014 (7 pages).
Pacifici et al., "Vitamin A inhibits chondrogenesis but not myogenesis," Exp Cell Res. 129(2):469-74 (1980) (Abstract Only).

Pacifici et al., Annual Report for U.S. Army Medical Research and Material Command, Oct. 2014, "Preventative Therapeutics for Heterotopic Ossification," (13 pages).
Pakala et al., "RAR gamma agonists inhibit proliferation of vascular smooth muscle cells," J Cardiovasc Pharmacol. 35(2):302-8 (2000) (Author manuscript) (17 pages).
Patent Examination Report No. 1 for New Zealand Patent Application No. 607547, dated Oct. 21, 2013 (3 pages).
Patent Examination Report No. 1 in Australian Patent Application No. 2011296080, dated Jul. 4, 2014 (4 pages).
Ray et al., "Signaling of c-kit in dendritic cells influences adaptive immunity," available in PMC May 2, 2013, published in final edited form as: Ann N.Y Acad Sci. 1183:104-22 (2010) (23 pages).
Rochette-Egly et al., "Dynamic and combinatorial control of gene expression by nuclear retinoic acid receptors (RARs)," Nuclear Receptor Signaling. 7:1-18 (2009).
Sanvitale et al., "A new class of small molecule inhibitor of BMP signaling," PLoS One. 8(4):e62721 (2013) (11 pages).
Schmale et al., "The natural history of hereditary multiple exostoses," J Bone Joint Surg Am. 76(7):986-92 (1994).
Schneider et al., "Activation of retinoic acid receptor alpha is sufficient for full induction of retinoid responses in SK-BR-3 and T47D human breast cancer cells," Cancer Res. 60(19):5479-87 (2000).
Seale et al., "The potential of muscle stem cells," Dev Cell. 1(3):333-42 (2001).
Second Office Action and English Comments for Chinese Patent Application No. 201180052926.X, dated Mar. 27, 2015 (12 pages).
Shimono et al., "A retinoid composition for rapid muscle repair and regeneration." Poster presented at BioTech 2010 Conference (Oct. 27, 2010).
Shimono et al., "Inhibition of ectopic bone formation by a selective retinoic acid receptor alpha-agonist: A new therapy for heterotopic ossification?," J Orthop Res. 28(2): 271-277 (2010).
Shimono et al., "Potent inhibition of heterotopic ossification by nuclear retinoic acid receptor-gamma agonists," Nat Med. 17(4):454-60 (2011).
Shiota et al., "The anti-allergic compound tranilast attenuates inflammation and inhibits bone destruction in collagen-induced arthritis in mice," Br J Pharmacol. 159(3):626-35 (2010).
Sinha et al., "Effectiveness and mode of action of a combination therapy for heterotopic ossification with a retinoid agonist and an anti-inflammatory agent," available in PMC Sep. 1, 2017, published in final edited form as: Bone. 90:59-68 (2016) (23 pages).
Sinha et al., "Unsuspected osteochondroma-like outgrowths in the cranial base of Hereditary Multiple Exostoses patients and modeling and treatment with a BMP antagonist in mice," PLoS Genet. 13(4):e1006742 (2017) (26 pages).
Soprano et al., "Role of retinoic acid in the differentiation of embryonal carcinoma and embryonic stem cells." Vitam Norm. 75:69-95 (2007).
Stolk et al., "Randomised controlled trial for emphysema with a selective agonist of the gamma-type retinoic acid receptor," Eur Respir J. 40(2):306-12 (2012).
Supplemental Figure S4 from Di Rocco et al., "Selective retinoic acid receptor gamma agonists promote repair of injured skeletal muscle in mouse," Am J Pathol. 185(9):2495-504 (2015) (2 pages).
Thacher et al., "Therapeutic applications for ligands of retinoid receptors," Curr Pharm Des. 6(1):25-58 (2000).
Third Office Action and English Comments for Chinese Patent Application No. 201180052926.X, dated Oct. 12, 2015 (11 pages).
Wang et al., "Bone Morphogenetic Protein (BMP) signaling in development and human diseases," Genes Dis. 1(1):87-105 (2014).
Wang et al., "Cellular Hypoxia Promotes Heterotopic Ossification by Amplifying BMP Signaling," J Bone Miner Res. 31(9):1652-65 (2016).
Weston et al., "Requirement for RAR-mediated gene repression in skeletal progenitor differentiation," J Cell Biol. 158(1):39-51 (2002).
Weston et al., "Revisiting the role of retinoid signaling in skeletal development," Birth Defects Res C Embryo Today. 69(2):156-73 (2003).

(56) References Cited

OTHER PUBLICATIONS

Williams et al., "Retinoic acid receptors are required for skeletal growth, matrix homeostasis and growth plate function in postnatal mouse," Dev Biol. 328(2):315-27 (2009).
Wozney et al., "Novel regulators of bone formation: molecular clones and activities," Science. 242(4885):1528-34 (1988).
Wuyts et al., "Hereditary Multiple Osteochondromas," GeneReviews, posted Aug. 3, 2000, last updated Nov. 21, 2013 (17 pages).
Yasuhara et al. "Wnt/beta-catenin and retinoic acid receptor signaling pathways interact to regulate chondrocyte function and matrix turnover." J Biol Chem. 285(1):317-327 (2010).
Yu et al., "BMP type I receptor inhibition reduces heterotopic [corrected] ossification," available in PMC Mar. 29, 2010, published in final edited form as: Nat Med. 14(12):1363-9 (2008) (14 pages).
Zasloff et al., "Treatment of patients who have fibrodysplasia ossificans progressiva with isotretinoin," Clin Orthop Relat Res. 346:121-9 (1998).

* cited by examiner

METHODS FOR TREATING MULTIPLE OSTEOCHONDROMA (MO)

RELATED APPLICATIONS

The present Patent Cooperation Treaty application claims priority to U.S. Application No. 62/423,019 filed on Nov. 16, 2016, which is herein incorporated by reference in its entirety.

BACKGROUND OF THE INVENTION

Multiple osteochondroma (MO) (also called multiple hereditary exostoses (MHE)) is a genetic musculoskeletal condition in which multiple bone spurs or lumps, also known as osteochondromas or exostoses, develop on bones. Osteochondromas in MO typically form at the end of long bones or on flat bones, such as the hip, shoulder blade or ribs. MO affects approximately 1 in 50,000 individuals. MO has been associated with loss-of-function mutations in EX1 and EX2 exostosin genes. Such mutations are thought to be causal in 90% of patients with MO. Osteochondromas associated with MO typically develop early in childhood; 50% of children with MO have visible osteochondromas by age five and 80% are diagnosed before age ten. MO causes crippling deformities and ankyloses of the joints. Patients with MO often undergo multiple surgeries to remove the osteochondromas. In 2-5% of patients with MO, osteochondromas become neoplastic. Efforts to prevent and/or slow the development of osteochondromas, and/or to improve treatment of subjects having MO have not been successful. There exists a need for new and effective treatments for MO.

SUMMARY OF THE INVENTION

The invention features methods for treating a subject with multiple osteochondroma (MO), a genetic disease associated with loss-of-function mutations in EX1 and EX2 exostosin genes.

The invention features methods for inhibiting the formation of an osteochondroma, reducing the size of an osteochondroma, and slowing the growth of an osteochondroma in a subject with multiple osteochondroma (MO), a genetic disease associated with loss-of-function mutations in EX1 and EX2 exostosin genes.

In one aspect, the invention features a method of inhibiting the formation of an osteochondroma in a subject with multiple osteochondroma (MO), including administering palovarotene ((E)-4-(2-{3-[(1H-pyrazole-1-yl)methyl]-5,5,8,8 tetramethyl-5,6,7,8-tetrahydronaphthalene-2-yl}vinyl)benzoic acid), or a pharmaceutically acceptable salt thereof, to the subject in an amount effective to inhibit the formation of the osteochondroma.

In another aspect, the invention features a method of reducing the size of an osteochondroma in a subject with MO, including administering palovarotene ((E)-4-(2-{3-[(1H-pyrazole-1-yl)methyl]-5,5,8,8 tetramethyl-5,6,7,8-tetrahydronaphthalene-2-yl}vinyl)benzoic acid), or a pharmaceutically acceptable salt thereof, to the subject in an amount effective to reduce the size of the osteochondroma. In some embodiments of this aspect of the invention, the method reduces the average size of osteochondromas in the subject.

In another aspect, the invention features a method of slowing the growth of an osteochondroma in a subject with MO, comprising administering palovarotene ((E)-4-(2-{3-[(1H-pyrazole-1-yl)methyl]-5,5,8,8 tetramethyl-5,6,7,8-tetrahydronaphthalene-2-yl}vinyl)benzoic acid), or a pharmaceutically acceptable salt thereof, to the subject in an amount effective to slow the growth of the osteochondroma. In some embodiments, the osteochondroma is formed adjacent to an area of bone growth. In some embodiments, the osteochondroma is formed adjacent to a growth plate. In some embodiments, the osteochondroma is formed on a perichondrium (e.g., on the groove of Ranvier of the perichondrium). In some embodiments, the osteochondroma is formed on an epiphysis of a bone.

In some embodiments, the osteochondroma is formed on a long bone. In some embodiments, the osteochondroma is formed at an end of the long bone. In some embodiments, the osteochondroma is formed on a flat bone. In some embodiments, the osteochondroma is formed on a hip bone, a shoulder blade, a rib, a femur, a tibia, a humerus, a fibula, a pelvic bone, or a vertebrate.

In some embodiments, the osteochondroma is formed on the surface of a bone. In some embodiments, the osteochondroma is formed in the diaphysis of a bone. In some embodiments, the osteochondroma originates from the growth plate.

In some embodiments, the method reduces the number of osteochondromas in the subject. In some embodiments, the method reduces the number of bones that have at least one osteochondroma in the subject.

In another aspect, the invention features a method of reducing cartilage hyperplasia in a subject with MO, including administering palovarotene ((E)-4-(2-{3-[(1H-pyrazole-1-yl)methyl]-5,5,8,8 tetramethyl-5,6,7,8-tetrahydronaphthalene-2-yl}vinyl)benzoic acid), or a pharmaceutically acceptable salt thereof, to the subject in an amount effective to reduce the cartilage hyperplasia.

In some embodiments of the aspects of the invention, the subject does not have an osteochondroma.

In some embodiments of the aspects of the invention, the amount of palovarotene administered to the subject is between 0.5 and 9 mg daily (e.g., between 1±0.5, 2±0.5, 3±0.5, 4±0.5, 5±0.5, 6±0.5, 7±0.5, 8±0.5, or 8.5±0.5 mg daily). In some embodiments of the aspects of the invention, the amount of palovarotene administered to a subject weighing from 5 to 20 kg is between 0.5 and 9 mg daily.

In some embodiments of the aspects of the invention, the amount of palovarotene administered to a subject weighing from 5 to 20 kg is between 1.0±0.5 and 3.0±0.5 mg daily.

In some embodiments of the aspects of the invention, the amount of palovarotene administered to a subject weighing from 10 to 20 kg is between 1.0±0.5 and 3.0±0.5 mg daily.

In some embodiments of the aspects of the invention, the amount of palovarotene administered to a subject weighing from 5 to 20 kg is 1.0±0.1 mg daily.

In some embodiments of the aspects of the invention, the amount of palovarotene administered to a subject weighing from 10 to 20 kg is 1.0±0.1 mg daily.

In some embodiments of the aspects of the invention, the amount of palovarotene administered to a subject weighing from 5 to 20 kg is 2.5±0.25 mg daily.

In some embodiments of the aspects of the invention, the amount of palovarotene administered to a subject weighing from 10 to 20 kg is 2.5±0.25 mg daily.

In some embodiments of the aspects of the invention, the amount of palovarotene administered to the subject is between 0.5 and 12 mg daily (e.g., between 1±0.5, 2±0.5, 3±0.5, 4±0.5, 5±0.5, 6±0.5, 7±0.5, 8±0.5, 9±0.5, 10±0.5, 11±0.5, or 11.5±0.5 mg daily). In some embodiments of the aspects of the invention, the amount of palovarotene administered to a subject weighing from 20 to 40 kg is between 0.5 and 12 mg daily.

In some embodiments of the aspects of the invention, the amount of palovarotene administered to a subject weighing from 20 to 40 kg is between 1.0±0.5 and 4.0±0.5 mg daily.

In some embodiments of the aspects of the invention, the amount of palovarotene administered to a subject weighing from 20 to 40 kg is 1.5±0.15 mg daily.

In some embodiments of the aspects of the invention, the amount of palovarotene administered to a subject weighing from 20 to 40 kg is 3.0±0.3 mg daily.

In some embodiments of the aspects of the invention, the amount of palovarotene administered to the subject is between 0.5 and 15 mg daily (e.g., between 1±0.5, 2±0.5, 3±0.5, 4±0.5, 5±0.5, 6±0.5, 7±0.5, 8±0.5, 9±0.5, 10±0.5, 11±0.5, 12±0.5, 13±0.5, 14±0.5, or 14.5±0.5 mg daily). In some embodiments of the aspects of the invention, the amount of palovarotene administered to a subject weighing from 40 to 60 kg is between 0.5 and 15 mg daily.

In some embodiments of the aspects of the invention, the amount of palovarotene administered to a subject weighing from 40 to 60 kg is between 2±0.5 and 5±0.5 mg daily.

In some embodiments of the aspects of the invention, the amount of palovarotene administered to a subject weighing from 40 to 60 kg is 2.0±0.2 mg daily.

In some embodiments of the aspects of the invention, the amount of palovarotene administered to a subject weighing from 40 to 60 kg is 4.0±0.4 mg daily.

In some embodiments of the aspects of the invention, the amount of palovarotene administered to the subject is between 0.5 and 20 mg daily (e.g., between 1±0.5, 2±0.5, 3±0.5, 4±0.5, 5±0.5, 6±0.5, 7±0.5, 8±0.5, 9±0.5, 10±0.5, 11±0.5, 12±0.5, 13±0.5, 14±0.5, 15±0.5, 16±0.5, 17±0.5, 18±0.5, 19±0.5, or 19.5±0.5 mg daily). In some embodiments of the aspects of the invention, the amount of palovarotene administered to a subject weighing more than 60 kg is between 0.5 and 20 mg daily.

In some embodiments of the aspects of the invention, the amount of palovarotene administered to a subject weighing more than 60 kg is between 2.0±0.5 and 6.0±0.5 mg daily.

In some embodiments of the aspects of the invention, the amount of palovarotene administered to a subject weighing more than 60 kg is 2.5±0.25 mg daily.

In some embodiments of the aspects of the invention, the amount of palovarotene administered to a subject weighing more than 60 kg is 5.0±0.5 mg daily.

In some embodiments of the aspects of the invention, the subject is a child or an adolescent who is not fully grown. In some embodiments, the child or adolescent has not achieved full skeletal maturity.

In some embodiments of the aspects of the invention, the long bone growth of the subject is maintained while the subject is treated. In some embodiments, the methods described herein do not cause any damage to the growth plate of the subject while the subject is treated. In some embodiments, the methods described herein do not interfere with the normal bone growth of the subject.

In some embodiments of the aspects of the invention, the method reduces bone morphogenic protein (BMP) level and/or BMP signaling in a perichondrium (e.g., in the groove of Ranvier of the perichondrium) of the subject. In some embodiments of the aspects of the invention, the method reduces BMP level and/or BMP signaling in an epiphysis of a bone of the subject. In some embodiments of the aspects of the invention, the method reduces BMP level and/or BMP signaling in an overgrown cartilage of the subject.

In some embodiments of the aspects of the invention, the subject has a mutant exostosin gene (e.g., a mutant Ext1, Ext2, or Ext3 gene).

Alternatively, in any of the methods described herein, palovarotene, or a pharmaceutically acceptable salt thereof, may be replaced by another retinoid acid receptor (RAR) agonist (e.g., an RARγ selective agonist or an RARγ/β selective agonist). Many retinoid acid receptor agonists are known in the art, as well as method for their synthesis and preparation. In some embodiments, the retinoid acid receptor agonist for use in the methods described herein is selected from those described in Bernard et al. (*Biochem. Biophys. Res. Commun.* 186:977-983, 1992), Thacher et al. (*Curr. Pharm. Des.* 6:25-58, 2000), Dallavalle and Zunino (*Expert Opin. Ther. Pat.* 15:1625-1635, 2005), Alaverez et al. (*Expert Opin. Ther. Pat.* 21:55-63, 2011), Le Maire et al. (*Curr. Top. Med. Chem.* 12:505-527, 2012), Marchwicka et al. (*Expert Opin. Ther. Pat.* 26:957-971, 2016), U.S. Pat. Nos. 5,231,113, 5,700,836, 5,750,693, 6,090,826, 6,344,463, 6,300,350, 6,331,570, 6,593,359, 6,777,418, 6,828,337, 7,148,245, 7,476,673, 7,807,708, 7,872,026, 8,049,034, 8,163,952, 8,362,082, 8,772,273, and 8,765,805, and US Patent Application Publication Nos. US20160250260, US20030092758, and US20070249710, each of which is incorporated by reference herein. The retinoid acid receptor agonists described in the aforementioned journal publications, US patents, and US patent application publications include those compounds listed in the Table A below.

In particular embodiments of any of the methods described herein, palovarotene, or a pharmaceutically acceptable salt thereof, may be replaced by any one of Compounds 1-152, or a pharmaceutically acceptable salt thereof, as listed in Table A below.

TABLE A

| Reference | Compound # | Compound structure and/or name |
|---|---|---|
| Bernard et al. | 1 | ![structure] (also known as CD 436) |

TABLE A-continued
| Reference | Compound # | Compound structure and/or name |
|---|---|---|
| Bernard et al. | 2 | 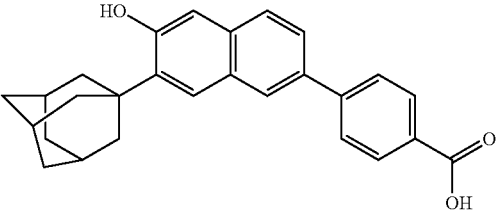<br>(also known as CD1530) |
| Bernard et al. | 3 | 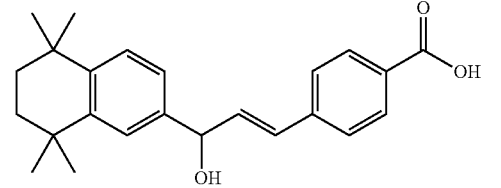<br>(also known as CD666) |
| Thacher et al. | 4 | 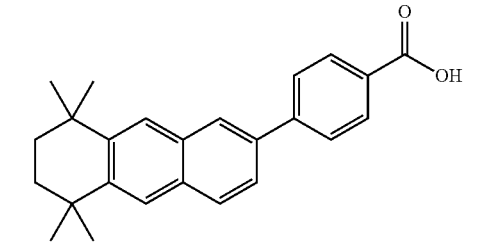<br>(also known as CD367) |
| Dallavalle and Zunino | 5 | 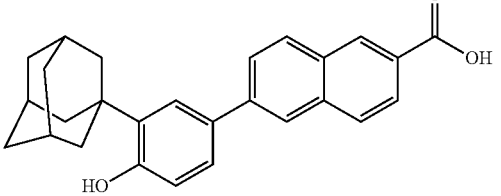<br>(also known as CD437) |
| Dallavalle and Zunino | 6 | 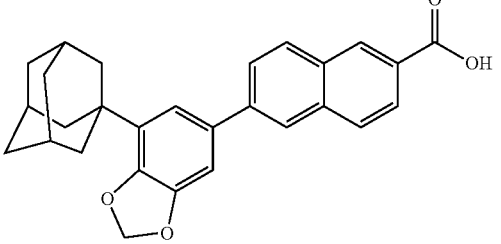<br>(also known as MX3350-1) |
| Dallavalle and Zunino | 7 | 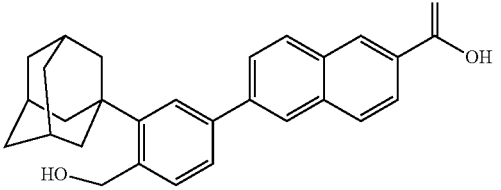<br>(also known as MX2870-1) |

TABLE A-continued
| Reference | Compound # | Compound structure and/or name |
|---|---|---|
| Dallavalle and Zunino | 8 | 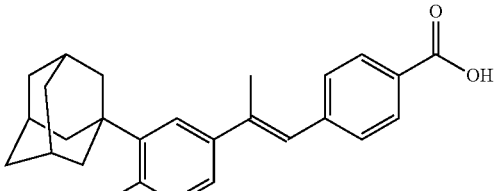<br>(also known as CD2325) |
| Dallavalle and Zunino | 9 | 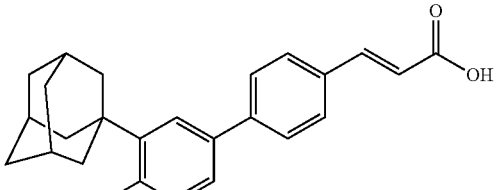<br>(also known as ST 1926) |
| Alaverez et al. | 10 | 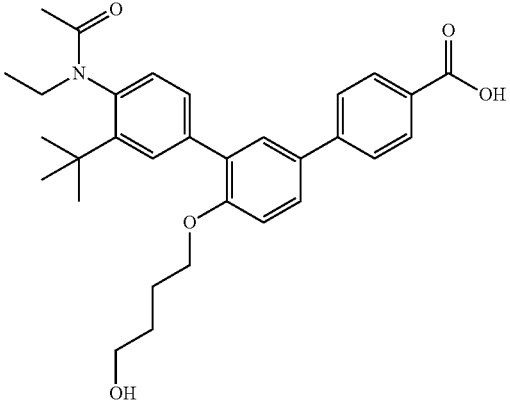<br>(also known as acetamide 15) |
| Alaverez et al. | 11 | 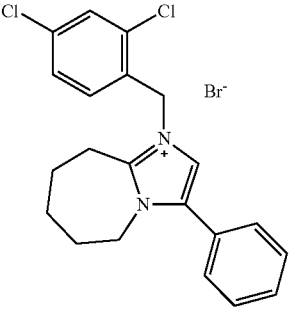<br>(also known as AC-41848) |
| Le Maire et al. | 12 | 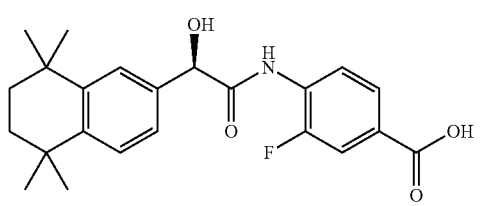 [SMILES: CC1(C)CCC(C)(C)c2cc([C@@H](O)C(=O)Nc3ccc(C(=O)O)cc3F)ccc21]<br>(also known as BMS270394) |

TABLE A-continued
| Reference | Compound # | Compound structure and/or name |
|---|---|---|
| Le Maire et al. | 13 | 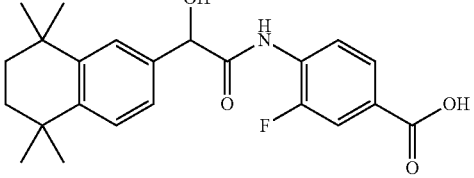<br>(also known as BMS189961) |
| Le Maire et al. | 14 | 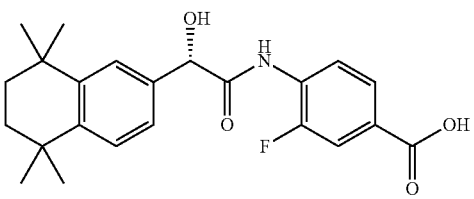<br>(also known as BMS270395) |
| Le Maire et al. | 15 | 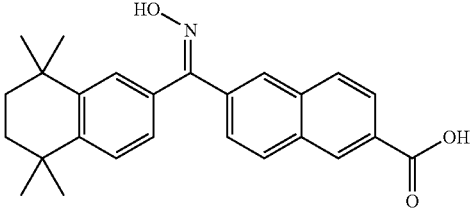<br>(also known as BMS185354 or SR11254) |
| Le Maire et al. | 16 | 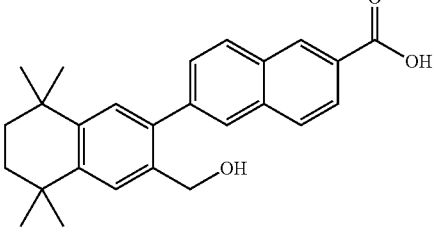 |
| Le Maire et al. | 17 | 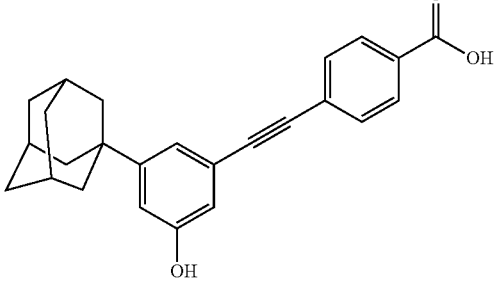 |
| Le Maire et al. | 18 | 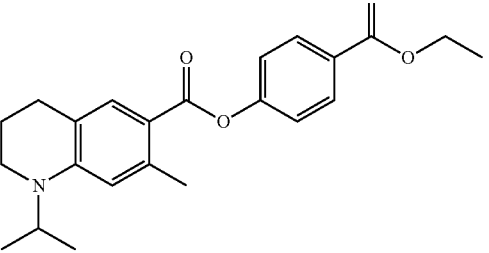 |

TABLE A-continued

| Reference | Compound # | Compound structure and/or name |
|---|---|---|
| Le Maire et al. | 19 | 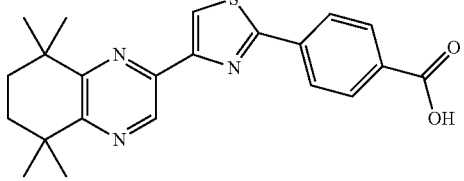 |
| Marchwicka et al. | 20 | 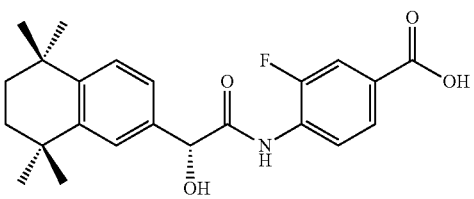<br>(also known as BMS961) |
| Marchwicka et al. | 21 | 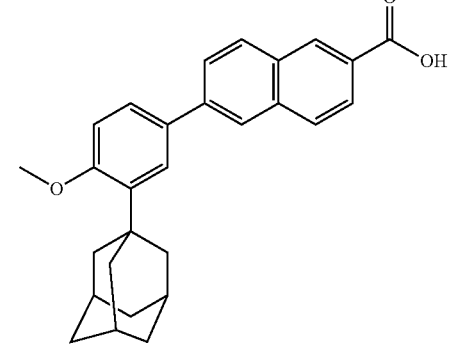<br>(also known as CD271) |
| U.S. Pat. No. 5,231,113 | 22 | ethyl 4-(5,5,8,8-tetramethyl-5,6,7,8-tetrahydro-2-naphthyl) terephthalate |
| U.S. Pat. No. 5,231,113 | 23 | (5,5,8,8-tetramethyl-5,6,7,8-tetrahydro-2-naphthyl) hydrogenterephthalate |
| U.S. Pat. No. 5,231,113 | 24 | benzyl (5,5,8,8-tetramethyl-5,6,7,8-tetrahydro-2-naphthyl) terephtallate |
| U.S. Pat. No. 5,700,836 | 25 | p-(E)-2-(3-hexyl-5,6,7,8-tetrahydro-5,5,8,8-tetramethyl-2-naphthyl)vinyl)benzoic acid |
| U.S. Pat. No. 5,700,836 | 26 | (E)-4-2-(3-Pentyl-5,5,8,8-tetramethyl-5,6,7,8-tetrahydro-naphthalen-2-yl)vinyl)benzoic acid |
| U.S. Pat. No. 5,700,836 | 27 | (E)-4-2-(3-Butyl-5,5,8,8-tetramethyl-5,6,7,8-tetrahydro-naphthalen-2-yl)vinyl)benzoic acid |
| U.S. Pat. No. 5,750,693, U.S. Pat. No. 6,090,826, and U.S. Pat. No. 6,344,463 | 28 | 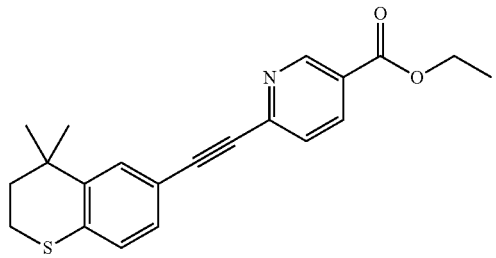<br>(also known as tazarotene (ethyl-6-[2-(4,4-dimethyl-thiochroman-6-yl)ethyl]nicotinate or tazarotenic acid) |
| U.S. Pat. No. 5,750,693, U.S. Pat. No. 6,090,826, and U.S. Pat. No. 6,344,463 | 29 | methyl 6-[2-(4,4-dimethyl-thiochroman-6-yl)ethyl]nicotinate |

TABLE A-continued

| Reference | Compound # | Compound structure and/or name |
|---|---|---|
| U.S. Pat. No. 5,750,693, U.S. Pat. No. 6,090,826, and U.S. Pat. No. 6,344,463 | 30 | i-propyl 6-[2-(4,4-dimethyl-thiochroman-6-yl)ethyl]nicotinate |
| U.S. Pat. No. 5,750,693, U.S. Pat. No. 6,090,826, and U.S. Pat. No. 6,344,463 | 31 | n-butyl 6-[2-(4,4-dimethyl-thiochroman-6-yl)ethyl]nicotinate |
| U.S. Pat. No. 7,476,673 | 32 | |
| U.S. Pat. No. 7,476,673 | 33 | |
| U.S. Pat. No. 7,476,673 | 34 | |
| U.S. Pat. No. 7,476,673 | 35 | |
| U.S. Pat. No. 7,476,673 | 36 | |
| U.S. Pat. No. 7,476,673 | 37 | |

TABLE A-continued

| Reference | Compound # | Compound structure and/or name |
|---|---|---|
| U.S. Pat. No. 7,807,708 | 38 | 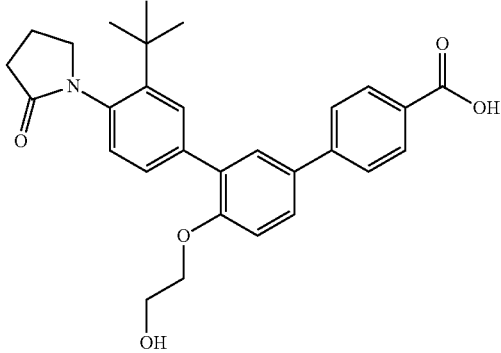<br>(also known as 3″-tert-butyl-4′-(2-hydroxyethoxy)-4″-(2-oxopyrrolidin-1-yl)-[1,1′;3′,1″]terphenyl-4-carboxylic acid) |
| U.S. Pat. No. 7,807,708 | 39 | 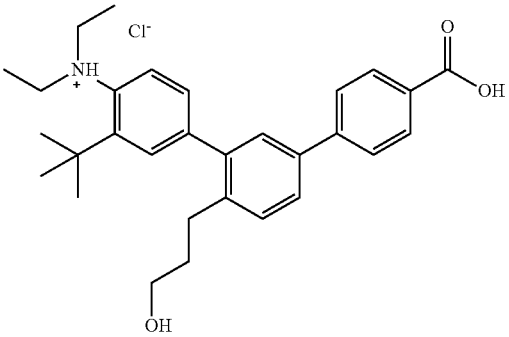<br>(also known as [3″-tert-butyl-4-carboxy-4′-(3-hydroxypropyl)-[1,1′;3′,1″]terphenyl-4″-yl]diethylamine hydrochloride) |
| U.S. Pat. No. 7,807,708 | 40 | 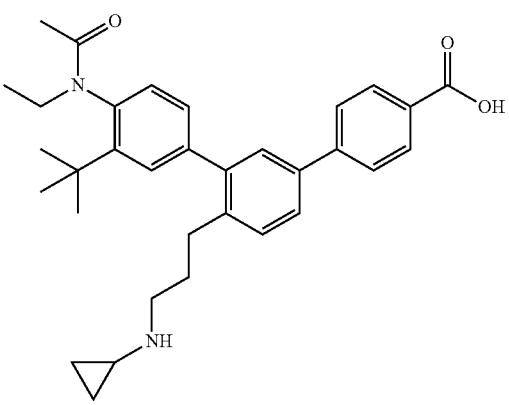<br>(also known as 4″-(acetylethylamino)-3″-tert-butyl-4′-(3-cyclopropylaminopropyl)-[1,1′;3′,1″]terphenyl-4-carboxylic acid) |

TABLE A-continued

| Reference | Compound # | Compound structure and/or name |
|---|---|---|
| U.S. Pat. No. 7,807,708 | 41 | 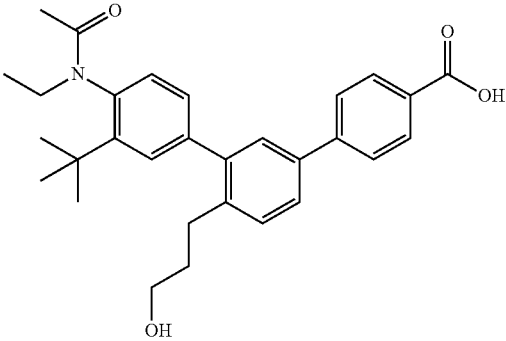<br>(also known as 4″-(acetylethylamino)-3″-tert-butyl-4′-(3-hydroxypropyl)-[1,1′;3′,1″]terphenyl-4-carboxylic acid) |
| U.S. Pat. No. 7,807,708 | 42 | 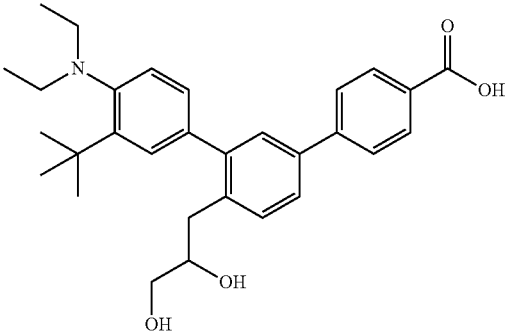<br>(also known as 3″-tert-butyl-4″-diethylamino-4′-(2,3-dihydroxypropyl)-[1,1′;3′,1″]terphenyl-4-carboxylic acid) |
| U.S. Pat. No. 7,807,708 | 43 | 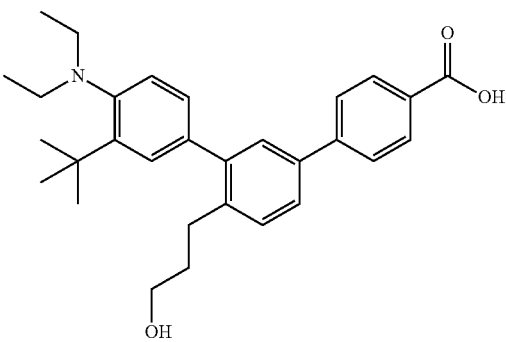<br>(also known as 3″-tert-butyl-4″-diethylamino-4′-(3-hydroxypropyl)-[1,1′;3′,1″]terphenyl-4-carboxylic acid) |

TABLE A-continued

| Reference | Compound # | Compound structure and/or name |
|---|---|---|
| U.S. Pat. No. 7,807,708 | 44 | 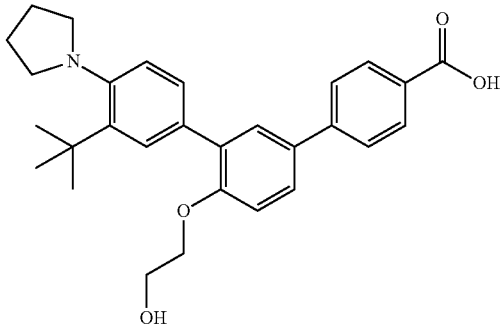<br>(also known as 3″-tert-butyl-4′-(2-hydroxyethoxy)-4″-pyrrolidin-1-yl[1,1′;3′,1″]terphenyl-4-carboxylic acid) |
| U.S. Pat. No. 7,807,708 | 45 | 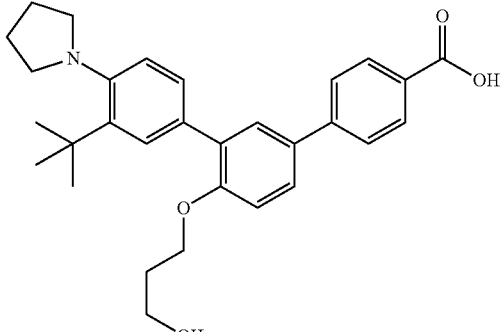<br>(also known as 3″-tert-butyl-4′-(3-hydroxypropoxy)-4″-pyrrolidin-1-yl[1,1′;3′,1″]terphenyl-4-carboxylic acid) |
| U.S. Pat. No. 7,807,708 | 46 | 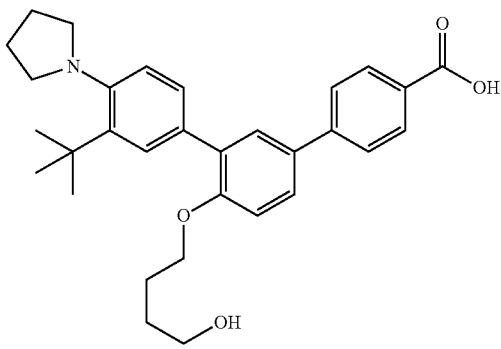<br>(also known as 3″-tert-butyl-4′-(4-hydroxybutoxy)-4″-pyrrolidin-1-yl[1,1′;3′,1″]terphenyl-4-carboxylic acid) |

TABLE A-continued

| Reference | Compound # | Compound structure and/or name |
|---|---|---|
| U.S. Pat. No. 7,807,708 | 47 | 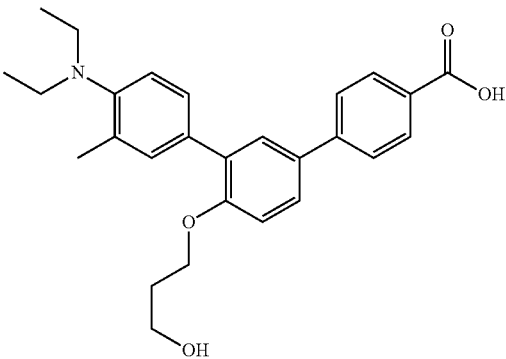<br>(also known as 4″-diethylamino-4′-(3-hydroxypropoxy)-3″-methyl[1,1′;3′,1″]terphenyl-4-carboxylic acid) |
| U.S. Pat. No. 7,807,708 | 48 | 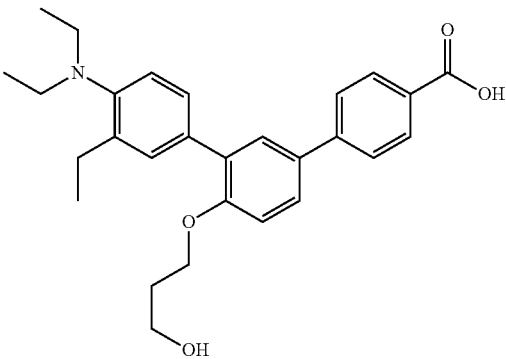<br>(also known as 4″-diethylamino-3″-ethyl-4′-(3-hydroxypropoxy)-[1,1′;3′,1″]terphenyl-4-carboxylic acid) |
| U.S. Pat. No. 7,807,708 | 49 | 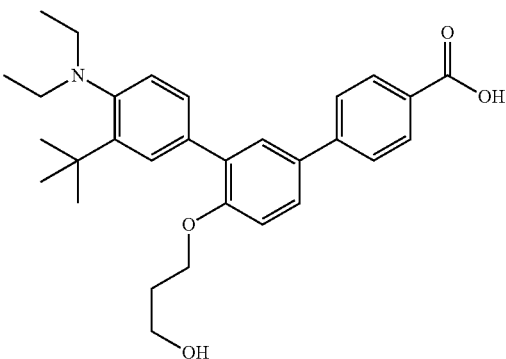<br>(also known as 3″-tert-butyl-4″-diethylamino-4′-(2-hydroxypropoxy)-[1,1′;3′,1″]terphenyl-4-carboxylic acid) |

TABLE A-continued

| Reference | Compound # | Compound structure and/or name |
|---|---|---|
| U.S. Pat. No. 7,807,708 | 50 | 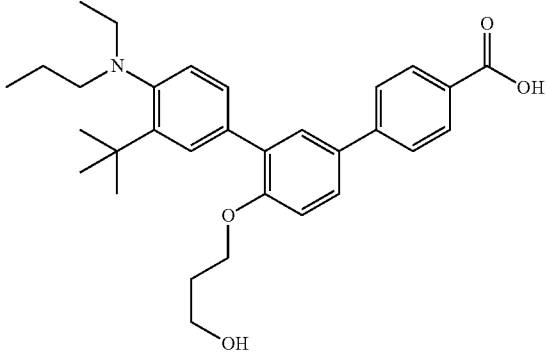<br>(also known as 3″-tert-butyl-4″-diethylamino-4′-(2-hydroxyethoxy)-[1,1′;3′,1″]terphenyl-4-carboxylic acid) |
| U.S. Pat. No. 7,807,708 | 51 | 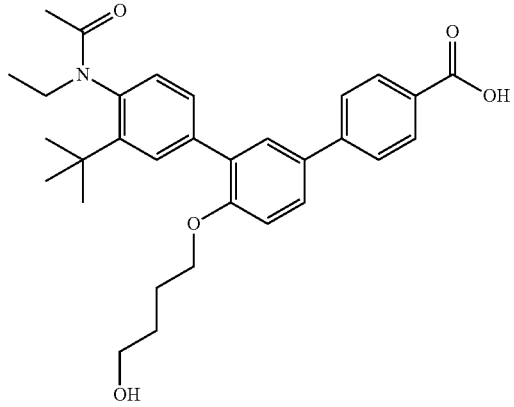<br>(also known as 4″-(acetylethylamino)-3″-tert-butyl-4′-(4-hydroxybutoxy)-[1,1′;3′,1″]terphenyl-4-carboxylic acid) |
| U.S. Pat. No. 7,807,708 | 52 | 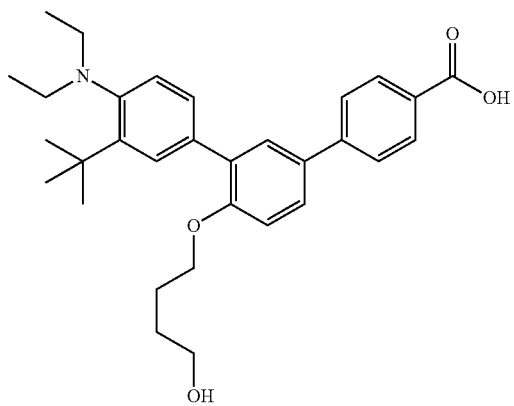<br>(also known as 3″-tert-butyl-4″-diethylamino-4′-(4-hydroxybutoxy)-[1,1′;3′,1″]terphenyl-4-carboxylic acid) |

TABLE A-continued

| Reference | Compound # | Compound structure and/or name |
|---|---|---|
| U.S. Pat. No. 6,300,350 | 53 | (chemical structure) |
| U.S. Pat. No. 6,593,359 | 54 | 6-3-(1-adamantyl)-4-hydroxyphenyl)-2-naphthanoic acid |
| U.S. Pat. No. 6,593,359 | 55 | (E)-4-(1-hydroxy-1-(5,6,7,8-tetrahydro-5,5,8,8-tetramethyl-2naphthyl)-2-propenyl)benzoic acid |
| U.S. Pat. No. 6,593,359 | 56 | 4-[(E)-2-(3-(1-adamantyl)-4-hydroxyphenyl)-1-propenyl]benzoic acid |
| U.S. Pat. No. 6,593,359 | 57 | 5',5',8',8'-tetramethyl-5',6',7',8'-tetrahydro-[2,2']binaphthalenyl-6-carboxylic acid |
| U.S. Pat. No. 6,593,359 | 58 | 2-(5,5,8,8-tetramethyl-5,6,7,8-tetrahydro-naphthalen-2-yl)-benzo[b]thiophene-6-carboxylic acid |
| U.S. Pat. No. 6,593,359 | 59 | 4-(5,5,8,8-tetramethyl-5,6,7,8-tetrahydro-naphtho[2,3-b]thiophen-2-yl)benzoic acid |
| U.S. Pat. No. 6,593,359 | 60 | 6-(5,5,8,8-tetramethyl-5,6,7,8-tetrahydro-naphthalene-2-carbonyl)naphthalene-2-carboxylic acid |
| U.S. Pat. No. 6,593,359 | 61 | 3,7-dimethyl-7-(1,2,3,4-tetrahydro-1,4a,9b-trimethyl-1,4-methano-dibenzofuran-8-yl)-2,4,6-heptatrienoic acid |
| U.S. Pat. No. 6,593,359 | 62 | 6-(1,2,3,4-tetrahydro-1,4a,9b-trimethyl-1,4-methano-dibenzofuran-8-yl)-naphthalene-2-carboxylic acid |
| U.S. Pat. No. 6,593,359 | 63 | 6-[hydroxyimino-(5,5,8,8-tetramethyl-5,6,7,8-tetrahydro-naphthalen-2-yl)-methyl]naphthalene-2-carboxylic acid |
| U.S. Pat. No. 6,593,359 | 64 | 4-[(6-hydroxy-7-(1-adamantyl)-2-naphthyl]benzoic acid, 5-(5,5,8,8-tetramethyl-5,6,7,8-tetrahydro-anthracen-2-yl)-thiophene-2-carboxylic acid |
| U.S. Pat. No. 6,593,359 | 65 | (−)-6-[hydroxy-(5,5,8,8-tetramethyl-5,6,7,8-tetrahydro-naphthalen-2-yl)-methyl]-naphthalene-2-carboxylic acid |
| U.S. Pat. No. 6,593,359 | 66 | 4-[(2-oxo-2-(5,5,8,8-tetramethyl-5,6,7,8-tetrahydro-naphthalen-2-yl)-ethoxy]-benzoic acid |
| U.S. Pat. No. 6,593,359 | 67 | 4-[2-oxo-2-(5,5,8,8-tetramethyl-5,6,7,8-tetrahydro-naphthalen-2-yl)-acetylamino]-benzoic acid |
| U.S. Pat. No. 6,593,359 | 68 | 4-[2-fluoro-2-(5,5,8,8-tetramethyl-5,6,7,8-tetrahydro-naphthalen-2-yl)-acetylamino]-benzoic acid, 6-[3-(1-adamantyl-4-(2-hydroxypropyl)phenyl]-2-naphthoic acid |
| U.S. Pat. No. 6,593,359 | 69 | 6-[3-(1-adamantyl-4-(2,3-di-hydroxypropyl)phenyl]-2-naphthoic acid |
| U.S. Pat. No. 6,593,359 | 70 | 4-[3-hydroxy-(5,6,7,8-tetrahydro-5,5,8,8-tetramethyl-2-naphthyl)-1-propynyl]-benzoic acid |
| U.S. Pat. No. 6,593,359 | 71 | 4-[3-oxo-3-(5,5,8,8-tetramethyl-5,6,7,8-tetrahydro-naphthalen-2-yl)-prop-1-ynyl]benzoic acid |
| U.S. Pat. No. 6,593,359 | 72 | 4-[(3-(1-methylcyclohexyl)-4-hydroxyphenyl)ethenyl]-benzoic acid, 4-[(E)2-(3-(1-adamantyl)-4-hydroxyphenyl)-ethenyl]-benzoic acid |
| U.S. Pat. No. 6,593,359 | 73 | 4-[3-(1-adamantyl)-4-hydroxyphenylethynyl]-benzoic acid |
| U.S. Pat. No. 6,593,359 | 74 | 5-[3-(1-adamantyl)-4-methoxyphenylethynyl]-2-thiophene-carboxylic acid |
| U.S. Pat. No. 6,593,359 | 75 | 5-[3-(1-adamantyl)-4-methoxyphenylethynyl]-2-thiophene-carboxylic acid |
| U.S. Pat. No. 6,593,359 | 76 | 4-[2-(3-tert-butyl-4-methoxyphenyl)-propenyl]benzoic acid |
| U.S. Pat. No. 6,593,359 | 77 | 4-{2-[4-methoxy-3-(1-methyl-cyclohexyl)phenyl]-propenyl}-benzoic acid |
| U.S. Pat. No. 6,593,359 | 78 | 6-[3-(1-adamantyl)-4-(3-methoxy-2-hydroxypropyl)-phenyl]-2-naphthoic acid |
| U.S. Pat. No. 6,593,359 | 79 | 2-hydroxy-4-[3-hydroxy-3-(5,6,7,8-tetrahydro-5,5,8,8-tetramethyl-2-naphthyl)-1-propynyl]-benzoic acid |
| U.S. Pat. No. 6,593,359 | 80 | 6-(5,5,8,8-tetramethyl-5,6,7,8-tetrahydro-naphthalen-2-yloxy)-naphthalene-2-carboxylic acid |
| U.S. Pat. No. 6,593,359 | 81 | 6-(5,5,8,8-tetramethyl-5,6,7,8-tetrahydro-naphthalen-2-ylsulphanyl)-naphthalene-2-carboxylic acid |
| U.S. Pat. No. 6,593,359 | 82 | 4-[2-propoxyimino-2-(5,5,8,8-tetramethyl-5,6,7,8-tetrahydro-naphthalen-2-yl)-acetylamino]benzoic acid |
| U.S. Pat. No. 6,593,359 | 83 | 6-(5,5,8,8-tetramethyl-5,6,7,8-tetrahydro-naphthalen-2-ylamino)naphthalene-2-carboxylic acid |
| U.S. Pat. No. 6,593,359 | 84 | 1-methyl-4-(5,5,8,8-tetramethyl-5,6,7,8-tetrahydroanthracen-2-yl)-1H-pyrrole-2-carboxylic acid |

TABLE A-continued

| Reference | Compound # | Compound structure and/or name |
|---|---|---|
| U.S. Pat. No. 6,593,359 | 85 | 2-methoxy-4-(5,5,8,8-tetramethyl-5,6,7,8-tetrahydro-anthracen-2-yl)-benzoic acid |
| U.S. Pat. No. 6,593,359 | 86 | 4-[2-nonyloxyimino-2-(5,5,8,8-tetramethyl-5,6,7,8-tetrahydro-naphthalen-2-yl)-acetylamino]-benzoic acid |
| U.S. Pat. No. 6,593,359 | 87 | (−)-2-hydroxy-4-[3-hydroxy-3-(5,5,8,8-tetramethyl-5,6,7,8-tetrahydro-naphthalen-2-yl)-prop-1-ynyl]-benzoic acid |
| U.S. Pat. No. 6,593,359 | 88 | (+)-2-hydroxy-4-[3-hydroxy-3-(5,5,8,8-tetramethyl-5,6,7,8-tetrahydro-naphthalen-2-yl)-prop-1-ynyl]-benzoic acid |
| U.S. Pat. No. 6,593,359 | 89 | 2-hydroxy-4-[3-hydroxy-3-(5,5,8,8-tetramethyl-5,6,7,8-tetrahydro-naphthalen-2-yl)-but-1-ynyl]-benzoic acid |
| U.S. Pat. No. 6,593,359 | 90 | 6-(3-bromo-5,5,8,8-tetramethyl-5,6,7,8-tetrahydro-naphthalen-2-yloxy)-naphthalene-2-carboxylic acid |
| U.S. Pat. No. 6,593,359 | 91 | 3-[(5,6,7,8-tetrahydro-5,5,8,8-tetramethyl-2-naphthyl)-2H-1-benzopyran]-7-carboxylic acid, 4-[3-(3,5-di-tert-butyl-4-hydroxy-phenyl)-prop-1-ynyl]-benzoic acid |
| U.S. Pat. No. 6,593,359 | 92 | 4-[3-(5,5,8,8-tetra-methyl-5,6,7,8-tetrahydro-naphthalen-2-yl)-prop-1-ynyl]-benzoic acid |
| U.S. Pat. No. 6,593,359 | 93 | 4-[3-(5,6,7,8-tetrahydro-5,5,8,8-tetramethyl-2-naphthyl)-1-propynyl]-salicylic acid |
| U.S. Pat. No. 6,593,359 | 94 | 4-[{3-(1-adamantyl)-4-(2-hydroxyethyl)phenyl}ethynyl]-benzoic acid |
| U.S. Pat. No. 6,593,359 | 95 | 4-[{3-(1-adamantyl)-4-(3-hydroxy-propyl)phenyl}ethynyl]-benzoic acid |
| U.S. Pat. No. 6,777,418 | 97 | <chemical structure> |
| U.S. Pat. No. 6,777,418 | 98 | <chemical structure> |
| U.S. Pat. No. 6,777,418 | 99 | <chemical structure> |

TABLE A-continued

| Reference | Compound # | Compound structure and/or name |
|---|---|---|
| U.S. Pat. No. 6,777,418 | 100 | |
| U.S. Pat. No. 6,777,418 | 101 | |
| U.S. Pat. No. 6,777,418 | 102 | |
| U.S. Pat. No. 6,777,418 | 103 | |
| U.S. Pat. No. 6,777,418 | 104 | |

TABLE A-continued

| Reference | Compound # | Compound structure and/or name |
|---|---|---|
| U.S. Pat. No. 6,331,570 | 105 | (structure: 2-(5,5,8,8-tetramethyl-5,6,7,8-tetrahydronaphthalen-2-yl)-2-hydroxy-N-(2-fluoro-4-carboxyphenyl)acetamide) |
| U.S. Pat. No. 7,148,245 | 106 | 3''-Methyl-2'-(5,5,8,8-tetramethyl-5,6,7,8-tetrahydronaphthalen-2-yl)-[1,1':4,1'']-tert-phenyl-4''-carboxylic acid (Example 41) |
| U.S. Pat. No. 7,148,245 | 107 | 3''-Hydroxy-2'-(5,5,8,8-tetramethyl-5,6,7,8-tetrahydronaphthalen-2-yl)-[1,1':4,1'']-tert-phenyl-4''-carboxylic acid (Example 46); and |
| U.S. Pat. No. 7,148,245 | 108 | 2''-Methoxy-2'-(5,5,8,8-tetramethyl-5,6,7,8-tetrahydronaphthalen-2-yl)-[1,1':4,1'']-tert-phenyl-4''-carboxylic acid (Example 44) |
| U.S. Pat. No. 6,828,337 | 109 | 4,4,7,7-tetramethyl-2,3,4,5,6,7-hexahydro-1H-indene-2-carboxylic acid 4-carboxy-phenyl ester |
| U.S. Pat. No. 6,828,337 | 110 | 2,4,4,7,7-pentamethyl-2,3,4,5,6,7-hexahydro-1H-indene-2-carboxylic acid 4-carboxy-phenyl ester |
| U.S. Pat. No. 6,828,337 | 111 | 2-ethyl-4,4,7,7-tetramethyl-2,3,4,5,6,7-hexahydro-1H-indene-2-carboxylic acid 4-carboxy-phenyl ester |
| U.S. Pat. No. 6,828,337 | 112 | 1 4,4,7,7-tetramethyl-2-pentyl-2,3,4,5,6,7-hexahydro-1H-indene-2-carboxylic acid 4-carboxy-phenyl ester |
| U.S. Pat. No. 6,828,337 | 113 | 2-benzyl-4,4,7,7-tetramethyl-2,3,4,5,6,7-hexahydro-1H-indene-2-carboxylic acid 4-carboxy-phenyl ester |
| U.S. Pat. No. 6,828,337 | 114 | 4-[2-(4,4,7,7-tetramethyl-2-pentyl-2,3,4,5,6,7-hexahydro-1H-indene-2-yl)-vinyl]-benzoic acid |
| U.S. Pat. No. 6,828,337 | 115 | 4-(4,4,7,7-tetramethyl-2-pentyl-2,3,4,5,6,7-hexahydro-1H-indene-2-ylethynyl)-benzoic acid |
| U.S. Pat. No. 7,872,026 | 116 | 4'-(4-Cyclopropylaminobutoxy)-3'-(5,5,8,8-tetramethyl-5,6,7,8-tetrahydronaphth-2-yl)biphenyl-4-carboxylic acid |
| U.S. Pat. No. 7,872,026 | 117 | 4'-(5-Cyclopropylaminopentyloxy)-3'-(5,5,8,8-tetramethyl-5,6,7,8-tetrahydronaphth-2-yl)biphenyl-4-carboxylic acid |
| U.S. Pat. No. 7,872,026 | 118 | 4'-(5-Aminopentyloxy)-3'-(5,5,8,8-tetramethyl-5,6,7,8-tetrahydronaphth-2-yl)biphenyl-4-carboxylic acid |
| U.S. Pat. No. 7,872,026 | 119 | 4'-(2-Cyclopropylaminoethoxy)-3'-(5,5,8,8-tetramethyl-5,6,7,8-tetrahydronaphth-2-yl)biphenyl-4-carboxylic acid |
| U.S. Pat. No. 8,049,034 and U.S. Pat. No. 8,362,082 | 120 | 4'-(3-hydroxypropoxy)-3'-(5,5,8,8-tetramethyl-5,6,7,8-tetrahydronaphthalen-2-yl)biphenyl-4-carboxylic acid |
| U.S. Pat. No. 8,049,034 and U.S. Pat. No. 8,362,082 | 121 | 4'-(4-hydroxybutoxy)-3'-(5,5,8,8-tetramethyl-5,6,7,8-tetrahydronaphthalen-2-yl)biphenyl-4-carboxylic acid |
| U.S. Pat. No. 8,163,952 | 122 | 4-[(tert-butyldiethylaminophenyl)hydroxyprop-1-ynyl]benzoic acid |
| U.S. Pat. No. 8,163,952 | 123 | 4-{[tert-butyl(ethylisobutylamino)phenyl]hydroxyprop-1-ynyl}benzoic acid |
| U.S. Pat. No. 8,163,952 | 124 | 4-[3-(3-tert-butyl-4-dimethylaminophenyl)-3-hydroxyprop-1-ynyl]benzoic acid |
| U.S. Pat. No. 8,163,952 | 125 | 4-[3-(3-tert-butyl-4-pyrrolidin-1-ylphenyl)-3-hydroxyprop-1-ynyl]benzoic acid |
| U.S. Pat. No. 8,163,952 | 126 | 4-[3-(3-tert-butyl-4-piperidin-1-ylphenyl)-3-hydroxyprop-1-ynyl]benzoic acid |
| U.S. Pat. No. 8,163,952 | 127 | 4-[3-(3-tert-butyl-4-diethylaminophenyl)-3-hydroxyprop-1-ynyl]-2-hydroxybenzoic acid |
| U.S. Pat. No. 8,163,952 | 128 | 4-[3-(3-tert-butyl-5-chloro-4-dimethylaminophenyl)-3-hydroxyprop-1-ynyl]benzoic acid |
| U.S. Pat. No. 8,163,952 | 129 | 4-[3-(3-tert-butyl-5-chloro-4-dimethylaminophenyl)-3-hydroxyprop-1-ynyl]-2-hydroxybenzoic acid |
| U.S. Pat. No. 8,163,952 | 130 | 4-[3-(4-dimethylamino-3,5-diisopropylphenyl)-3-hydroxyprop-1-ynyl]benzoic acid |
| U.S. Pat. No. 8,163,952 | 131 | 4-[3-(4-dimethylamino-3,5-diisopropylphenyl)-3-hydroxyprop-1-ynyl]-2-hydroxybenzoic acid |
| U.S. Pat. No. 8,163,952 | 132 | 4-[3-(4-diethylamino-3-isopropylphenyl)-3-hydroxyprop-1-ynyl]benzoic acid |
| U.S. Pat. No. 8,163,952 | 133 | 4-[3-(3-tert-butyl-4-diethylaminophenyl)-3-hydroxyprop-1-ynyl]benzoic acid |
| U.S. Pat. No. 8,765,805 | 134 | 4-{3-Hydroxy-3-[4-(2-ethoxyethoxy)-6,5,8,8-tetramethyl-5,6,7,8-tetrahydronaphth-2-yl]prop-1-ynyl}benzoic acid |
| U.S. Pat. No. 8,765,805 | 135 | 4-{3-Hydroxy-3-[4-(2-methoxyethoxy)-5,5,8,8-tetramethyl-5,6,7,8-tetrahydronaphth-2-yl]prop-1-ynyl}benzoic acid |
| US20160250260 | 136 | NRX204647 (4-((1E,3E)-3-(hydroxyimino)-3-(5,5,8,8-tetramethyl-5,6,7,8-tetrahydronaphthalen-2-yl)prop-1-en-1-yl)benzoic acid) |

TABLE A-continued

| Reference | Compound # | Compound structure and/or name |
|---|---|---|
| US20160250260 | 137 | all-trans 3-4 didehydro retinoic acid |
| US20160250260 | 138 | 4-[(E)-2-(5,6,7,8-tetrahydro-5,5,8,8-tetramethyl-2-naphthalenyl)-1-propenyl]benzoic acid |
| US20160250260 | 139 | 4-(5-methoxymethyl-5-methyl-2,3,4,5-tetrahydro-1-benzo[b]oxepin-8-yl-ethynyl)-benzoic acid |
| US20160250260 | 140 | 4-(5-ethoxymethyl-5-methyl-2,3,4,5-tetrahydrobenzo[b]oxepin-8-ylethynyl)-benzoic acid |
| US20160250260 | 141 | 4-(5-methyl-5-propoxymethyl-2,3,4,5-tetrahydrobenzo[b]oxepin-8-ylethynyl)-benzoic acid |
| US20160250260 | 142 | (E)-4-[2-(5-methoxymethyl-5-propyl-2,3,4,5-tetrahydrobenzo[b]oxepin-8-yl)-vinyl]-benzoic acid |
| US20160250260 | 143 | (E)-4-[2-(5-methoxymethyl-5-methyl-2,3,4,5-tetrahydrobenzo[b]oxepin-8-yl)-vinyl]-benzoic acid |
| US20160250260 | 144 | (E)-4-[2-(5-methyl-5-propoxymethyl-2,3,4,5-tetrahydrobenzo[b]oxepin-8-yl)-vinyl]-benzoic acid |
| US20160250260 | 145 | 4-(5-methoxymethyl-5-methyl-2,3,4,5-tetrahydrobenzo[b]thiepin-8-ylethynyl)-benzoic acid |
| US20160250260 | 146 | 4-(5-ethoxymethyl-5-methyl-2,3,4,5-tetrahydrobenzo[b]thiepin-8-ylethynyl)-benzoic acid |
| US20160250260 | 147 | (E)-4-[2-(5-ethoxymethyl-5-methyl-2,3,4,5-tetrahydrobenzo[b]thiepin-8-yl)-vinyl]-benzoic acid |
| US20160250260 | 148 | (E)-4-[2-(5-methoxymethyl-5-propyl-2,3,4,5-tetrahydrobenzo[b]thiepin-8-yl)-vinyl]-benzoic acid |
| US20160250260 | 149 | 4-(4-methoxymethyl-4-methyl-chroman-6-ylethynyl)-benzoic acid |
| US20160250260 | 150 | (E)-4-[2-(4-methoxymethyl-4-methyl-chroman-6-yl)-vinyl]-benzoic acid |
| US20030092758 | 151 | 6-[3-(adamantan-1-yl)-4-(prop-2-ynyloxy)phenyl]napthalene-2-carboxylic acid |
| US20030092758 | 152 | 5-[(E)-3-oxo-3-(5,5,8,8-tetrahydronaphthalene-2-yl)propenyl]thiophene-2-carboxylic acid |

In some embodiments, the retinoid acid receptor (RAR) agonist used in the methods described herein has an RAR over RXR selectivity that is greater than 3 (e.g., 3, 4, 5, 6, 7, 8, 9, 10, 11, 12, 13, 14, 15, 16, 17, 18, 19, or 20).

In some embodiments, the retinoid acid receptor agonist used in the methods described herein has an RARγ over RARβ selectivity that is between 3 and 10 (e.g., 3, 4, 5, 6, 7, 8, 9, or 10) and/or an RARγ over RARα selectivity that is greater than 10 (e.g., 10, 11, 12, 13, 14, 15, 16, 17, 18, 19, or 20).

In certain embodiments of the invention, the RARγ selective agonist has a RAR selectivity such that:

(i) the ratio of its EC50 for RARβ ($EC50_{RAR\beta}$) to its EC50 for RARγ ($EC50_{RAR\gamma}$) is between 3 and 15 e.g., $EC50_{RAR\beta}/EC50_{RAR\gamma}$ for the RARγ selective agonist is between 3 and 15 or between 3 and 10, and (ii) the ratio of its EC50 for RARα ($EC50_{RAR\alpha}$) to its EC50 for RARγ ($EC50_{RAR\gamma}$) is greater than 10 e.g., $EC50_{RAR\alpha}/EC50_{RAR\gamma}$ for the RARγ selective agonist is greater than 10.

Methods for identifying or evaluating an RAR selective agonist (e.g., an RARγ selective agonist or an RARγ/β selective agonist) are known in the art. For example, the binding activity of an RARγ agonist may be evaluated using a transactivation assay. As used herein, the term "transactivation" refers to the ability of a retinoid to activate the transcription of a gene where the gene transcription is initiated by the binding of a ligand to the particular retinoic acid receptor being tested, e.g., RARα, RARβ, or RARγ. Determining the ability of a compound to transactivate a retinoic acid receptor may be performed by methods known to those of skill in the art. Examples of such methods are found in the art, see, e.g., Bernard et al., *Biochem. Biophys. Res. Commun.*, 186: 977-983, 1992 and Apfel et al., *Proc. Nat. Sci. Acad. (USA)*, 89: 7129-7133, 1992. Using the transactivation assay, the EC50 of a compound for a retinoic acid receptor (e.g., RARα, RARβ, or RARγ) can be determined. EC50 in a transactivation assay refers to the molar concentration of the compound which transactivates the particular retinoic acid receptor under consideration by 50% of the maximum transactivation which can be obtained with the same compound. The EC50 of an RARγ selective agonist for either the RARα or the RARβ is at least 3 fold higher (e.g., at least 3, 4, 5, 6, 7, 8, 9, 10, 11, 12, 13, 14, 15, 16, 17, 18, 19, or 20 fold higher) than the EC50 of the same RARγ selective agonist for the RARγ in the same assay system. In some embodiments, the EC50 of an RARγ selective agonist for RARα is at least 10 fold higher (e.g., at least 10, 20, 30, 40, 50, 60, 70, 80, 90, 100 fold higher) than the EC50 of the same RARγ selective agonist for the RARγ in the same assay system.

For example, in a transactivation assay, cells stably transfected with plasmids for the ERE-13Glob-Luc-SV-Neo (REF) reporter gene and chimeric RAR (e.g., RARα, RARβ, or RARγ) ER-DBD-puro receptors. Upon agonist binding, the chimeric RAR-ER-DBD binds to the ERE-βGlob-Luc which controls the transcription of the luciferase (Luc). Similar methods are described in the art (see, e.g., US20030092758A1, ¶[0081]). One of skill in the art can also easily determine whether a compound is an RARγ agonist (e.g., an RARγ selective agonist) by measuring binding affinities between the compound and various RAR, e.g., RARα, RARβ, and RARγ. Binding affinities can be determined using conventional techniques in the art, e.g., radioligand binding assay, surface plasmon resonance, enzyme-linked immunosorbent assay (ELISA), gel electrophoresis, immunoblots, and mass spectrometry.

In some embodiments, the retinoid acid receptor (RAR) agonist is an RAR selective agonist having an RAR selectivity that is between 3 and 10 (e.g., 3, 4, 5, 6, 7, 8, 9, or 10) relative to retinoid X receptor (RXR) receptors. In some embodiments, the RAR agonist is an RAR selective agonist having an RAR selectivity that is at least 10 (e.g., 10, 11, 12, 13, 14, 15, 16, 17, 18, 19, or 20) relative to RXR receptors.

Definitions

As used herein, the term "multiple osteochondroma" or "MO" refers to a condition or disease associated with formation of osteochondromas on bones, e.g., at the ends of long bones or on flat bones. Subjects with MO often carry a loss-of-function mutation in an exostosin gene, e.g., Ext1, Ext2, or Ext3 gene. MO is also known as multiple hereditary exostoses (MHE), Bessel-Hagen disease, diaphyseal aclasis, multiple cartilaginous exostoses, multiple congenital exostosis, and hereditary multiple osteochondroma (HMO), and such terms can be used interchangeably.

As used herein, the term "osteochondroma," "osteochondromas," "exosostosis," "exostoses," "cartilaginous exostosis," or "osteocartilaginous exostosis" refers to bony or bone-like structures or projections formed from cartilaginous lesions that ossified. Osteochondromas may form on the surface of a bone, but in some cases may migrate to the diaphysis of the bone. In subjects with MO, such bony or bone-like structures or projections often form adjacent to areas of active bone growth, e.g., near the growth plates of bones. In some embodiments, osteochondromas can form on long bones (e.g., at an end of a long bone) or on flat bones. In some embodiments, osteochondromas can form on a hip bone, a shoulder blade, a rib, a femur, a tibia, a humerus, a fibula, a pelvic bone, or a vertebrate. The invention describes methods for inhibiting the formation of an osteochondroma, reducing the size of an osteochondroma, and slowing the growth of an osteochondroma that forms on a bone of a subject with MO.

Osteochondromas often cause deformities of the skeletal system, such as short stature, limb length inequalities, bowing of the limb bones, ankyloses, and scoliosis. In some embodiments, osteochondromas contain a cartilaginous cap overlaying a bony base. In some embodiments, osteochondromas may undergo a malignant transformation into metastatic chondrosarcoma.

As used herein, the phrase "inhibiting the formation of an osteochondroma" refers to inhibiting the formation of an osteochondroma in a subject with MO, e.g., a subject with MO who already developed one or more osteochondromas, or a subject with MO who has not developed any osteochondromas. Inhibiting the formation of an osteochondroma includes reducing by at least 5%, 10%, 20%, or 50% the number of osteochondromas formed in subjects undergoing a treatment of the invention relative to untreated subjects.

As used herein, the phrase "reducing the size of an osteochondroma" refers to reducing the size of an already existing osteochondroma and/or reducing the average size of osteochondromas in a subject with MO with a number of existing osteochondromas. Reducing the size of an osteochondroma includes reducing by at least 5%, 10%, 20%, or 50% the size of an osteochondroma, or reducing the average size of osteochondromas in a subject by at least 5%, 10%, 20%, or 50%, in subjects undergoing a treatment of the invention relative to untreated subjects.

As used herein, the phrase "slowing the growth of an osteochondroma" refers to slowing or stopping the growth of an already existing osteochondroma in a subject with MO. Slowing the growth of an osteochondroma includes reducing the growth of an osteochondroma by at least 5%, 10%, 20%, or 50% in subjects undergoing a treatment of the invention relative to untreated subjects.

The methods described herein may reduce the number of osteochondromas formed (e.g., the number of osteochondromas formed on one or more bones in a subject with MO), or the number of sites at which an osteochondroma is formed (e.g., the number of bones that have at least one osteochondroma in a subject with MO), in a palovarotene treated subject with MO over a given time period relative to an untreated subject with MO over the same time period. Methods described herein may ameliorate or inhibit bone deformations and/or other complications in the subject, e.g., joint deformation, limited mobility or range of motion, short stature, limb length inequalities, bowed bones, osteoarthritis, pain, ankyloses, scoliosis, entrapment of blood vessels, nerves, and/or tendons, and spinal cord compression.

As used herein, the term "cartilage hyperplasia" refers to an overgrowth or enlargement of the cartilage. The phrase "reducing cartilage hyperplasia" refers to the reduction in size or thickness of the overgrown or enlarged cartilage.

As used herein, the term "overgrown cartilage" refers to a cartilage that has grown or developed to be larger than its normal size.

As used herein, the term "fully grown" is used to describe a person or animal that is fully matured and is no longer developing or growing. When a person is fully grown, he or she has reached his or her full natural growth or development.

As used herein, the term "skeletal maturity" refers to the degree of maturation of a person's bones. The bones of a person change size and shape as the person grows from fetal life through childhood, puberty, and finishes growth as an adult. Full skeletal maturity is used to describe the full maturation of a person's bones when the bones have reached their full natural growth and have stopped growing. A person has not reached or achieved full skeletal maturity if his or her bones are still growing.

As used herein, the term "normal bone growth" refers to the growth (e.g., increasing in size) of a person's bones during the normal course of the person's natural, physiological development as the person matures from an infant or a child to an adult.

As used herein, the term "retinoic acid receptor (RAR) selective agonist" or "RAR agonist" refers to a compound that selectively binds to (e.g., activates or agonizes) an RAR (e.g., RARα, RARβ, or RARγ) relative to a retinoid X receptor (RXR) (e.g., RXRα, RXRβ, or RXRγ) (e.g., RAR over RXR selectivity), and promotes RAR activation. RAR agonists bind to the RAR at significantly lower concentrations (e.g., lower EC50) than to the RXR. In some embodiments, an RAR agonist displays a greater than 3-fold selectivity (e.g., greater than 3-, 4-, 5-, 6-, 7-, 8-, 9-, 10-, 11-, 12-, 13-, 14-, 15-, 16-, 17-, 18-, 19-, or 20-fold selectivity) for the RAR than for the RXR.

As used herein, the term "RARγ selective agonist" or "RARγ agonist" refers to a compound that selectively binds to (e.g., activates or agonizes) the RARγ relative to the RARα or the RARβ (e.g., RARγ over RARβ selectivity and RARγ over RARα selectivity), and promotes RARγ activation. RARγ agonists bind to the RARγ at significantly lower concentrations (e.g., lower EC50) than to the RARα or the RARβ.

In some embodiments, an RARγ agonist displays a greater than 3-fold selectivity (e.g., greater than 3-, 4-, 5-, 6-, 7-, 8-, 9-, or 10-fold selectivity) for the RARγ than for the RARα or the RARβ. In some embodiments, an RARγ agonist displays a greater than 3-fold selectivity (e.g., greater than 3-, 4-, 5-, 6-, 7-, 8-, 9-, or 10-fold selectivity) for the RARγ than for the RARβ. In some embodiments, an RARγ agonist displays a greater than 10-fold selectivity (e.g., greater than 10-, 20-, 30-, 40-, 50-, 60-, 70-, 80, 90 or 100-fold selectivity) for the RARγ than for the RARα.

As used herein, the term "RARγ/β selective agonist" or "RARγ/β agonist" refers to a compound that selectively binds to (e.g., activates or agonizes) the RARγ and the RARβ relative to the RARα (e.g., RARγ over RARα selectivity and RARβ over RARα selectivity), and promotes RARγ and RARβ activation. RARγ/β agonists bind to the RARγ and the RARβ at significantly lower concentrations (e.g., lower EC50) than to the RARα. In some embodiments, an RARγ/β agonist displays a greater than 3-fold selectivity (e.g., greater than 3-, 4-, 5-, 6-, 7-, 8-, 9-, or 10-fold selectivity) for the RARγ than for the RARα and a greater than 3-fold selectivity (e.g., greater than 3-, 4-, 5-, 6-, 7-, 8-, 9-, or 10-fold selectivity) for the RARβ than for the RARα.

As used herein, the term "RAR over RXR selectivity" is defined as the ratio of the EC50 of a compound for the RXR to the EC50 of the compound for the RAR (e.g., $EC50_{RXR}/EC50_{RAR}$).

As used herein, the term "RARγ over RARβ selectivity" is defined as the ratio of the EC50 of a compound for the RARβ to the EC50 of the compound for the RARγ (e.g., $EC50_{RARβ}/EC50_{RARγ}$). In some embodiments, the RARγ selective agonist has an $EC50_{RARβ}/EC50_{RARγ}$ of between 3 and 15 or between 3 and 10.

As used herein, the term "RARγ over RARα selectivity" is defined as the ratio of the EC50 of a compound for the RARα to the EC50 of the compound for the RARγ (e.g., $EC50_{RARα}/EC50_{RARγ}$).

As used herein, the term "RARβ over RARα selectivity" is defined as the ratio of the EC50 of a compound for the RARα to the EC50 of the compound for the RARβ (e.g., $EC50_{RARα}/EC50_{RARβ}$). In some embodiments of the invention the RARγ selective agonist has an $EC50_{RARα}/EC50_{RARβ}$ of greater than 10.

In some embodiments, in any of the selectivity ratios described above (e.g., $EC50_{RXR}/EC50_{RAR}$, $EC50_{RARβ}/EC50_{RARγ}$, $EC50_{RARα}/EC50_{RARγ}$, and $EC50_{RARα}/EC50_{RARβ}$), the selectivity ratio may be greater 3 (e.g., greater than 3, 4, 5, 6, 7, 8, 9, 10, 11, 12, 13, 14, 15, 16, 17, 18, 19, or 20).

In some embodiments of the invention, the RARγ/β selective agonist has an $EC50_{RARβ}/EC50_{RARγ}$ of between 3 and 15 or between 3 and 10 and an $EC50_{RARα}/EC50_{RARβ}$ of greater than 10.

DETAILED DESCRIPTION OF THE INVENTION

Figure 1:
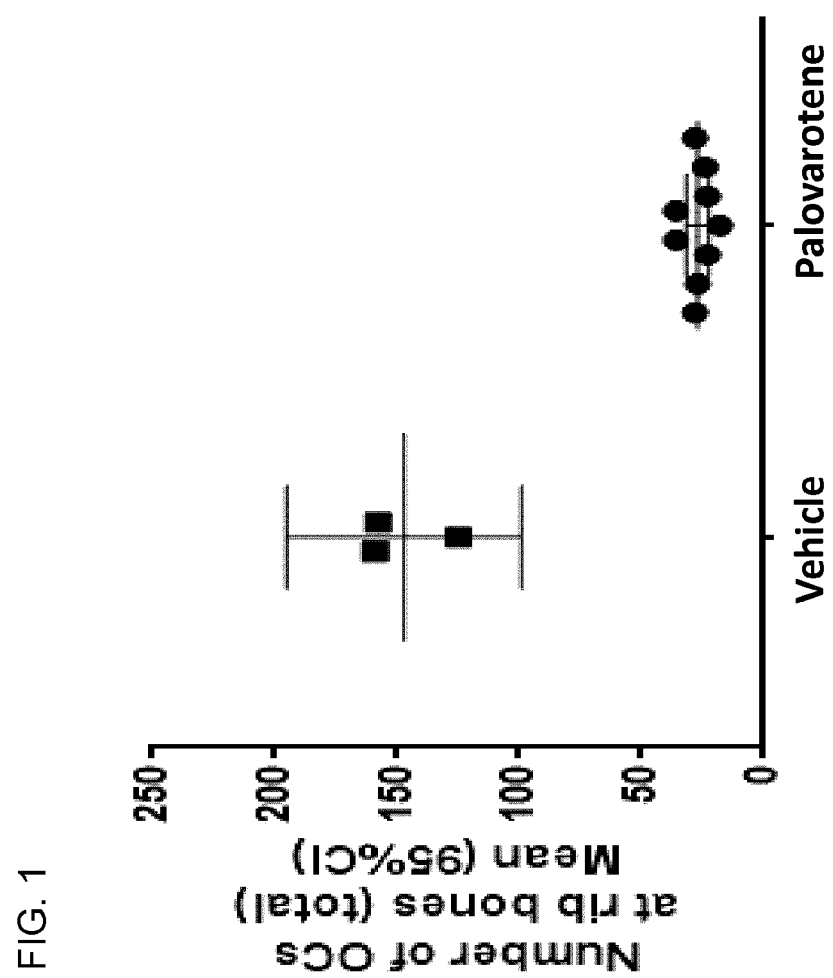
FIG. 1 is a graph showing the effect of palovarotene treatment on total number of osteochondromas (OCs) by alcian blue whole-mount skeletal staining at the rib bones in Fsp1-Ext1$^{CKO}$ mice.

The invention features methods for inhibiting the formation of an osteochondroma, reducing the size of an osteochondroma, and slowing the growth of an osteochondroma in a subject with multiple osteochondroma (MO) by administering to the subject palovarotene (also known as R667). The methods described herein can also ameliorate complications associated with osteochondroma formation and growth in a subject with MO.

I. Multiple Osteochondroma (MO)

Multiple osteochondroma (MO) is a genetic disease characterized by the development of osteochondromas, which are bony or bone-like structures or projections formed from cartilaginous lesions that ossified. Osteochondromas may form on the surface of a bone. In some embodiments, the osteochondromas originate from the growth plate. Osteochondromas are typically not present at birth, but a large percentage of individuals with MO develop visible osteochondromas by age five and are often diagnosed by age ten. Genetic linkage analysis has identified three genes as being associated with MO: Ext1, located on chromosome 8q24.1, Ext2, located on chromosome 11p11, and Ext3, linked to chromosome 19p. It has been established that EXT1 and EXT2 jointly encode a glycosyltransferase essential for heparan sulfate synthesis. Heparan sulfate is a highly sulfated linear polysaccharide with a backbone of alternating N-acetylglucosamine (GlcNAc) and glucuronic acid (GlcA) residues. The EXT1 and EXT2 proteins form an oligomeric complex that catalyzes the copolymerization of GlcNAc and GlcA residues, thereby elongating the heparan sulfate backbone. MO is also known as multiple hereditary exostoses (MHE), Bessel-Hagen disease, diaphyseal aclasis, multiple cartilaginous exostoses, multiple congenital exostosis, and hereditary multiple osteochondroma (HMO), and such terms can be used interchangeably.

Any joint or bone in the body can be affected by MO. In the subjects with MO, osteochondromas often form adjacent to areas of active bone growth, e.g., near the growth plates of bones. In some embodiments, osteochondromas can form on long bones (e.g., at an end of a long bone) or on flat bones. In some embodiments, osteochondromas can form on a hip bone, a shoulder blade, a rib, a femur, a tibia, a humerus, a fibula, a pelvic bone, or a vertebrate. In some embodiments, osteochondromas contain a cartilaginous cap overlaying a bony base. In some embodiments, osteochondromas may migrate from the surface of a bone to the diaphysis of the bone. In some embodiments, the osteochondromas originate from the growth plate. The number of osteochondromas and the bones on which they form may vary greatly among affected individuals. The methods described herein envision inhibiting the formation, reducing the size, and slowing the growth of all types of osteochondromas that form and grow in a subject with MO. Methods of the invention can be evaluated as described in Example 1.

Osteochondromas often cause deformities of the skeletal system, such as short stature, limb length inequalities, bowing of the limb bones, ankyloses, and scoliosis. In some embodiments, osteochondromas may undergo a malignant transformation into metastatic chondrosarcoma. In some embodiments, subjects having a mutant gene associated with MO (e.g., a mutant Ext1, Ext2, or Ext3 gene) do not have osteochondroma formation.

II. Methods of the Invention

The methods described herein include administering to a subject with MO a therapeutically effective amount of palovarotene, or a pharmaceutically acceptable salt thereof, to inhibit the formation, reduce the size, and slow the growth of an osteochondroma in the subject. The methods described herein also reduce cartilage hyperplasia in a subject with MO by administering to the subject palovarotene, or a pharmaceutically acceptable salt thereof, in an amount effective to reduce the cartilage hyperplasia. Palovarotene (4-[(1E)-2-[5,6,7,8-Tetrahydro-5,5,8,8-tetramethyl-3-(1H-pyrazol-1-ylmethyl)-2-naphthalenyl]-ethenyl]-benzoic acid; also known as R667) is a retinoic acid receptor gamma/beta (RARγ/β) selective agonist having the structure:

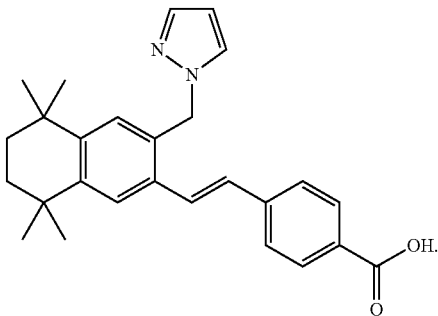 [SMILES: CC1(C)CCC(C)(C)c2cc(Cn3cccn3)c(/C=C/c3ccc(C(=O)O)cc3)cc21]

In some embodiments, the methods described herein inhibit the formation, reduce the size, and slow the growth of an osteochondroma formed adjacent to areas of active bone growth, e.g., near the growth plates of bones. In some embodiments, the methods described herein inhibit the formation, reduce the size, and slow the growth of an osteochondroma formed on long bones (e.g., at an end of a long bone) or on flat bones. In some embodiments, the methods described herein inhibit the formation, reduce the size, and slow the growth of an osteochondroma formed on a hip bone, a shoulder blade, a rib, a femur, a tibia, a humerus, a fibula, a pelvic bone, or a vertebrate of a subject with MO. In some embodiments, the methods described herein inhibit the formation, reduce the size, and slow the growth of an osteochondroma formed on a perichondrium of a subject with MO. In some embodiments, the methods described herein inhibit the formation, reduce the size, and slow the growth of an osteochondroma formed on the groove of Ranvier of the perichondrium of a subject with MO. In some embodiments, the methods described herein inhibit the formation, reduce the size, and slow the growth of an osteochondroma formed on an epiphysis of a bone of a subject with MO.

In some embodiments, the methods described herein inhibit the formation, reduce the size, and slow the growth of an osteochondroma that contain a cartilaginous cap overlaying a bony base. In some embodiments, the methods described herein inhibit the formation, reduce the size, and slow the growth of an osteochondroma that have migrated from the surface of a bone to the diaphysis of the bone. The methods described herein envision inhibiting the formation, reducing the size, and slowing the growth of all types of osteochondromas that form and grow in a subject with MO.

In some embodiments, the methods described herein reduce or slow the growth of one or more already existing osteochondromas in a subject with MO. In some embodiments, the methods reduce the size of one or more already existing osteochondromas in a subject with MO. In some embodiments, the methods reduce the average size of multiple osteochondromas in a subject with MO. Furthermore, the methods described herein may inhibit the formation of any new osteochondromas in a subject with MO.

In some embodiments, palovarotene, or a pharmaceutically acceptable salt thereof, may be administered to a subject having a genetic mutation associated with MO (e.g., a mutant Ext1, Ext2, or Ext3 gene) and has developed one or more osteochondromas. In other embodiments, palovarotene, or a pharmaceutically acceptable salt thereof, may be administered to a subject having a genetic mutation associated with MO (e.g., a mutant Ext1, Ext2, or Ext3 gene) and has not developed any osteochondromas.

The methods of the invention may reduce the number of osteochondromas that form (e.g., number of osteochondromas formed at rib bones), or the number of sites at which an osteochondroma is formed (e.g., number of rib bones showing at least one osteochondroma; see Example 1). For example, as shown in Example 1, the mean total number of osteochondromas at the rib bones was significantly lower in palovarotene treated Fsp1-Ext1$^{CKO}$ mice (mouse model of MO) than in vehicle treated mice. Example 1 also shows that the number of rib bones showing at least one osteochondroma is significantly lower in palovarotene treated mice than in vehicle treated mice.

The methods described herein also reduce cartilage hyperplasia or cartilage overgrowth in a subject with MO by administered to the subject palovarotene, or a pharmaceutically acceptable salt thereof, in an amount effective to reduce the cartilage hyperplasia or cartilage overgrowth.

In some embodiments of the methods described herein, the subject with MO who is treated by any of the methods is a child or an adolescent who is not fully grown. In some embodiments, the child or adolescent has not achieved skeletal maturity.

In some embodiments of the methods described herein, long bone growth of the subject is maintained and not affected by the treatment while the subject is treated.

In some embodiments, the methods described herein do not cause any damage to the growth plate of the subject while the subject is treated.

In some embodiments, the methods described herein do not interfere with the normal bone growth of the subject.

In some embodiments, the methods described herein may reduce bone morphogenic protein (BMP) level and/or BMP signaling in a perichondrium of a subject with MO. In some embodiments, the methods described herein may reduce BMP level and/or BMP signaling in the groove of Ranvier of the perichondrium of a subject with MO. In some embodiments, the methods described herein may reduce BMP level and/or BMP signaling in an epiphysis of a bone of a subject with MO. In some embodiments, the methods described herein may reduce BMP level and/or BMP signaling in an overgrown cartilage of the subject.

The methods described herein may also ameliorate or inhibit bone deformations and/or other complications in the subject, e.g., joint deformation, limited mobility or range of motion, short stature, limb length inequalities, bowed bones, osteoarthritis, pain, ankyloses, scoliosis, entrapment of blood vessels, nerves, and/or tendons, and spinal cord compression.

III. Pharmaceutical Composition and Formulation

For administration to a subject, palovarotene, or a pharmaceutically acceptable salt thereof, can be provided in pharmaceutically acceptable compositions. These pharmaceutically acceptable compositions include palovarotene, or a pharmaceutically acceptable salt thereof, and one or more pharmaceutically acceptable carriers and excipients. Pharmaceutical compositions may be formulated for administration in solid or liquid form.

The palovarotene can be administered in neutral form (i.e., the free base or zwitterionic neutral form). Optionally, palovarotene may be administered as a pharmaceutically acceptable salt, such as a non-toxic acid addition salts or metal complexes that are commonly used in the pharmaceutical industry. Examples of acid addition salts that could be used in the methods of the invention include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes that could be used in the methods of the invention include calcium, zinc, and iron, among others.

In some embodiments, a pharmaceutical composition including palovarotene, or a pharmaceutically acceptable salt thereof, is prepared for oral administration. In some embodiments, a pharmaceutical composition is formulated by combining palovarotene, or a pharmaceutically acceptable salt thereof, with one or more pharmaceutically acceptable carriers and excipients. Such carriers and excipients enable the pharmaceutical composition to be formulated as tablets, pills, dragees, capsules, liquids, gels, syrups, slurries, and suspensions, for oral ingestion by a subject.

In some embodiments, pharmaceutical compositions for oral use are obtained by mixing palovarotene, or a pharmaceutically acceptable salt thereof, and one or more carriers and excipients. Suitable carriers and excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, such a mixture is optionally ground and auxiliaries are optionally added. In some embodiments, pharmaceutical compositions are formed to obtain tablets or dragee cores. In some embodiments, disintegrating agents (e.g., cross-linked polyvinyl pyrrolidone, agar, or alginic acid or a salt thereof, such as sodium alginate) are added.

When palovarotene, or a pharmaceutically acceptable salt thereof, is administered orally, a pharmaceutical composition containing palovarotene, or a pharmaceutically acceptable salt thereof, may be in unit dosage form (e.g., liquid or solid unit dosage form). The concentration and/or amount of palovarotene, or a pharmaceutically acceptable salt thereof, in the formulation may vary depending on, e.g., the dosage of palovarotene, or a pharmaceutically acceptable salt thereof, to be administered and the frequency of administration.

In some embodiments, a pharmaceutical composition including palovarotene, or a pharmaceutically acceptable salt thereof, is prepared for administration to the skin of the subject as an emollient.

IV. Therapy and Dosage

In some embodiments, palovarotene, or a pharmaceutically acceptable salt thereof, is co-administered with one or more other pharmaceutical agents. In some embodiments, such one or more other pharmaceutical agents are designed to treat MO. In some embodiments, such one or more other pharmaceutical agents are designed to treat a disease or condition other than MO. In some embodiments, such one or more other pharmaceutical agents are designed to treat an undesired effect of palovarotene, or a pharmaceutically acceptable salt thereof. In some embodiments, palovarotene, or a pharmaceutically acceptable salt thereof, and one or more other pharmaceutical agents are administered at the same time. In some embodiments, palovarotene, or a pharmaceutically acceptable salt thereof, and one or more other pharmaceutical agents are administered at different times. For example, palovarotene, or a pharmaceutically acceptable salt thereof, may be administered first, followed by the administration of one or more other pharmaceutical agents. In some embodiments, one or more other pharmaceutical agents may be administered first, followed by the administration of palovarotene, or a pharmaceutically acceptable salt thereof. In some embodiments, palovarotene, or a pharmaceutically acceptable salt thereof, and one or more other pharmaceutical agents are prepared together in a single formulation. In some embodiments, palovarotene, or a pharmaceutically acceptable salt thereof, and one or more other pharmaceutical agents are prepared separately.

In some embodiments, palovarotene, or a pharmaceutically acceptable salt thereof, is administered in the form of a dosage unit (e.g., tablet, capsule, etc.). In some embodiments, palovarotene, or a pharmaceutically acceptable salt thereof, is administered in a dose between 0.5 and 20 mg (e.g., 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mg).

In one embodiment, a subject diagnosed as having MO and weighing 5 to 20 kg is administered palovarotene, or a pharmaceutically acceptable salt thereof, at a dose of between 0.5 and 9 mg daily (e.g., 0.5, 1, 1.5, 2, 2.5, 3, 3.5, 4, 4.5, 5, 5.5, 6, 6.5, 7, 7.5, 8, 8.5, or 9 mg daily).

In one embodiment, a subject diagnosed as having MO and weighing 5 to 20 kg is administered palovarotene, or a pharmaceutically acceptable salt thereof, at a dose of between 1.0±0.5 and 3.0±0.5 mg daily.

In one embodiment, a subject diagnosed as having MO and weighing 5 to 20 kg is administered palovarotene, or a pharmaceutically acceptable salt thereof, at a dose of between 1.0±0.5 and 3.0±0.5 mg daily.

In one embodiment, a subject diagnosed as having MO and weighing 5 to 20 kg is administered palovarotene, or a pharmaceutically acceptable salt thereof, at a dose of 1.0 mg daily.

In one embodiment, a subject diagnosed as having MO and weighing 5 to 20 kg is administered palovarotene, or a pharmaceutically acceptable salt thereof, at a dose of 1.0 mg daily.

In one embodiment, a subject diagnosed as having MO and weighing 5 to 20 kg is administered palovarotene, or a pharmaceutically acceptable salt thereof, at a dose of 2.5 mg daily.

In one embodiment, a subject diagnosed as having MO and weighing 5 to 20 kg is administered palovarotene, or a pharmaceutically acceptable salt thereof, at a dose of 2.5 mg daily.

In one embodiment, a subject diagnosed as having MO and weighing 5 to 20 kg is administered palovarotene, or a pharmaceutically acceptable salt thereof, at a dose of between 0.5 and 9 mg daily (e.g., 0.5, 1, 1.5, 2, 2.5, 3, 3.5, 4, 4.5, 5, 5.5, 6, 6.5, 7, 7.5, 8, 8.5, or 9 mg daily).

In one embodiment, a subject diagnosed as having MO and weighing 10 to 20 kg is administered palovarotene, or a pharmaceutically acceptable salt thereof, at a dose of between 1.0±0.5 and 3.0±0.5 mg daily.

In one embodiment, a subject diagnosed as having MO and weighing 10 to 20 kg is administered palovarotene, or a pharmaceutically acceptable salt thereof, at a dose of between 1.0±0.5 and 3.0±0.5 mg daily.

In one embodiment, a subject diagnosed as having MO and weighing 10 to 20 kg is administered palovarotene, or a pharmaceutically acceptable salt thereof, at a dose of 1.0 mg daily.

In one embodiment, a subject diagnosed as having MO and weighing 10 to 20 kg is administered palovarotene, or a pharmaceutically acceptable salt thereof, at a dose of 1.0 mg daily.

In one embodiment, a subject diagnosed as having MO and weighing 10 to 20 kg is administered palovarotene, or a pharmaceutically acceptable salt thereof, at a dose of 2.5 mg daily.

In one embodiment, a subject diagnosed as having MO and weighing 10 to 20 kg is administered palovarotene, or a pharmaceutically acceptable salt thereof, at a dose of 2.5 mg daily.

In one embodiment, a subject diagnosed as having MO and weighing 20 to 40 kg is administered palovarotene, or a pharmaceutically acceptable salt thereof, at a dose of between 0.5 and 12 mg daily (e.g., 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, or 12 mg daily).

In one embodiment, a subject diagnosed as having MO and weighing 20 to 40 kg is administered palovarotene, or a pharmaceutically acceptable salt thereof, at a dose of between 1.0±0.5 and 4.0±0.5 mg daily.

In one embodiment, a subject diagnosed as having MO and weighing 20 to 40 kg is administered palovarotene, or a pharmaceutically acceptable salt thereof, at a dose of 1.5 mg daily.

In one embodiment, a subject diagnosed as having MO and weighing 20 to 40 kg is administered palovarotene, or a pharmaceutically acceptable salt thereof, at a dose of 3.0 mg daily.

In another embodiment, a subject diagnosed as having MO and weighing 40 to 60 kg is administered palovarotene, or a pharmaceutically acceptable salt thereof, at a dose of between 0.5 and 15 mg daily (e.g., 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 mg daily).

In another embodiment, a subject diagnosed as having MO and weighing 40 to 60 kg is administered palovarotene, or a pharmaceutically acceptable salt thereof, at a dose of between 2±0.5 and 5±0.5 mg daily.

In another embodiment, a subject diagnosed as having MO and weighing 40 to 60 kg is administered palovarotene, or a pharmaceutically acceptable salt thereof, at a dose of 2.0 mg daily.

In another embodiment, a subject diagnosed as having MO and weighing 40 to 60 kg is administered palovarotene, or a pharmaceutically acceptable salt thereof, at a dose of 4.0 mg daily.

In a further embodiment, a subject diagnosed as having MO and weighing more than 60 kg is administered palovarotene, or a pharmaceutically acceptable salt thereof, at a dose of between 0.5 and 20 mg daily (e.g., 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mg daily).

In a further embodiment, a subject diagnosed as having MO and weighing more than 60 kg is administered palovarotene, or a pharmaceutically acceptable salt thereof, at a dose of between 2±0.5 and 6±0.5 mg daily.

In a further embodiment, a subject diagnosed as having MO and weighing more than 60 kg is administered palovarotene, or a pharmaceutically acceptable salt thereof, at a dose of 2.5 mg daily.

In a further embodiment, a subject diagnosed as having MO and weighing more than 60 kg is administered palovarotene, or a pharmaceutically acceptable salt thereof, at a dose of 5.0 mg daily.

In some embodiments, the dose can be administered once a day. In some embodiments, the dose can be administered more than once a day (e.g., twice a day or three times a day) at intervals (e.g., once every 4-8 hours, e.g., once every 4, 5, 6, 7, or 8 hours). In some embodiments, the dose can be administered once every two to 10 days (e.g., once every two days, once every three days, once every four days, once every five days, once every six days, once every seven days, once every eight days, once every nine days, or once every ten days). In some embodiments, the amount of palovarotene, or a pharmaceutically acceptable salt thereof, administered to the subject may increase or decrease from one dose to the next. In some embodiments, palovarotene, or a pharmaceutically acceptable salt thereof, may be administered to the subject with MO for as long as needed to sustain the desired effect.

EXAMPLES

Example 1—Effects of Palovarotene on Osteochondromas in a MO Mouse Model

Biallelic conditional knock-out (CKO) of Ext1 using a Cre transgene driven by an Fsp1 promotor) (Fsp1-Ext1$^{CKO}$ in mice leads to the formation of phenotypes characteristic of MO. Fsp1 expression in developing bone is restricted to the perichondrium and periosteum. Perichondrium-targeted Ext1 deletion in mice causes osteochondromatogenesis in long bones, vertebrae and ribs. Fsp1-Ext1$^{CKO}$ mice appear normal at birth, present mild bone deformity by P (postnatal day) 28 and have normal life span. In these mice, bony protrusions consisting of bony tuberosities with a cartilage cap are first detectable after P14. These protrusions are consistent with the histological features of osteochondromas in human MO. By P28, all animals develop multiple osteochondromas that can be readily observed in whole-mount skeletal preparations. This phenotype supports the relevance of the Fsp1-Ext1$^{CKO}$ mouse as a preclinical model of MO. It also mimics the findings observed in a previously developed mouse model of MO, the Col2a1-Ext1$^{CKO}$ mice.

The therapeutic effect of palovarotene in MO was tested in the Fsp1-Ext1$^{CKO}$ mouse model. The CKO mice were treated with palovarotene (1.05 mg/kg) or vehicle by oral gavage daily. Treatment was initiated on day 14 postpartum and continued daily for 4 weeks. The effect of palovarotene on the formation of osteochondromas (OCs) in the mouse model was evaluated using whole-mount skeletal preparation. At end of treatment, the mice were euthanized by $CO_2$ inhalation and the carcasses were eviscerated and fixed in 95% ethanol overnight. The preparations were stained with alcian blue for 3 days, rinsed in 95% ethanol, and incubated in 2% KOH for 1-2 days. Stained preparations were cleaned in 20% glycerol/1% KOH for 14 days and transferred to 50% glycerol/50% ethanol for photography and storage. By examination under a dissecting microscope, an alcian blue-positive protrusion that was clearly distinguishable was considered as an OC. OCs were identified and counted in each of the 24 rib bones from each mouse.

The sum of these counts (total number of OCs at the rib bones) and the mean occurrence of response (number of rib bones showing no OCs vs. number of rib bones showing at least one OC) were reported for each treatment group.

In vehicle treated Fsp1-Ext1$^{CKO}$ mice (n=3), 100% of the animals showed presence of OCs at all rib bones after 4 weeks of treatment. In vehicle treated Fsp1-Ext1$^{CKO}$ mice, the mean total number of OCs at the rib bones was significantly greater than in palovarotene treated Fsp1-

Figure 2:
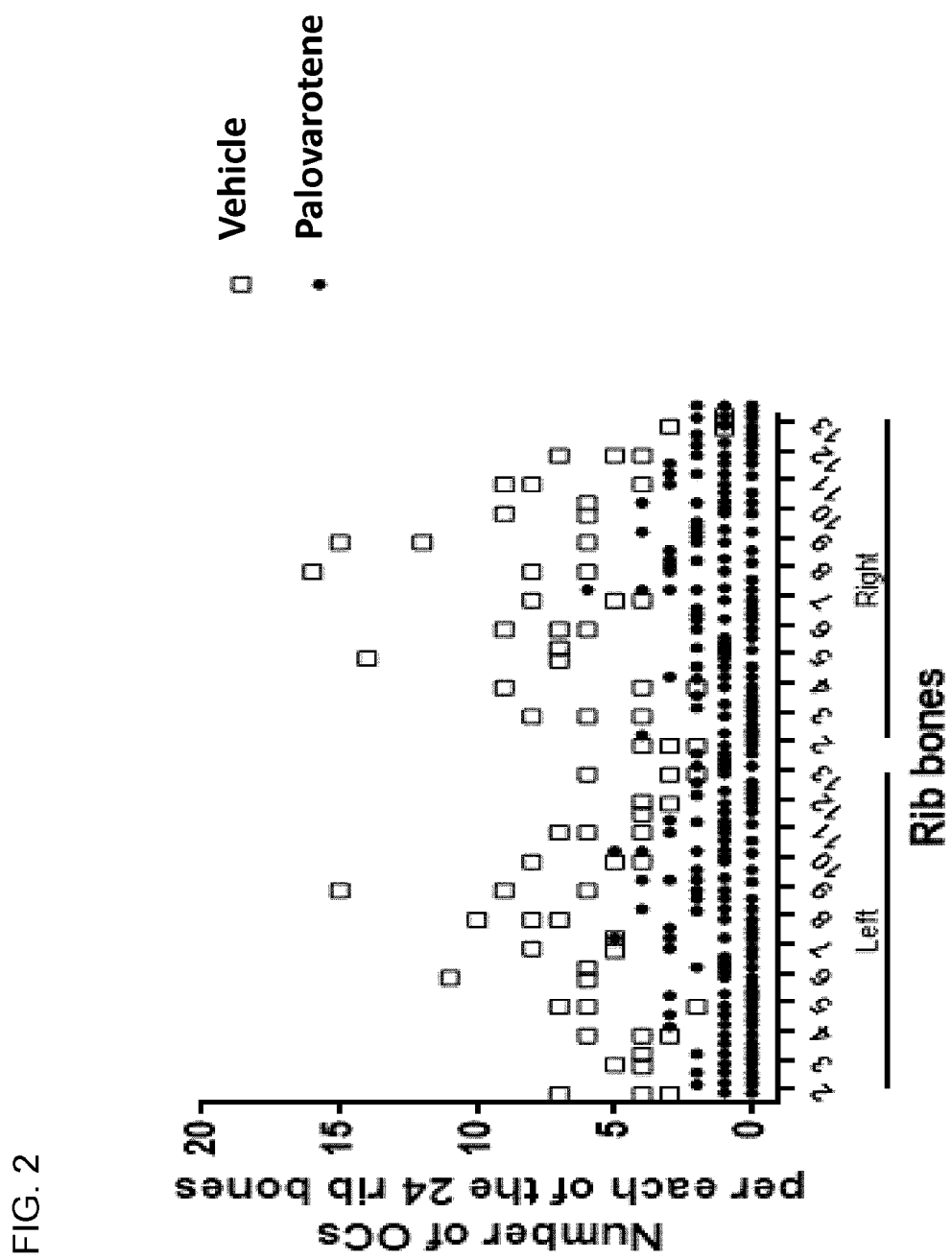
FIG. 2 is a graph showing the effect of palovarotene treatment on number of OCs by alcian blue whole-mount skeletal staining per each of 24 rib bones in Fsp1-Ext1$^{CKO}$ mice.

Ext1$^{CKO}$ mice (n=9), as presented in Table 1 and FIG. 1. Results showed that palovarotene treatment reduced the total number of OCs per rib bone and prevent the formation of OCs in Fsp1-Ext1$^{CKO}$ mice: no OCs were observed at some of the rib bones in palovarotene treated mice compared to vehicle treated mice in which all rib bones showed at least one OC (FIG. 2). Comparison of the mean occurrence of response (number of rib bones showing no OCs vs. number of rib bones showing at least one OC) using the Fisher's exact test suggested that the difference between palovarotene treatment and vehicle treatment is statistically significant (p=0.0039, Table 2). Taken together, these results suggest potential beneficial therapeutic effects of palovarotene in Fsp1-Ext1$^{CKO}$ mice, a mouse model of MO.

TABLE 1

Mean and 95% CI of total number of OCs by alcian blue whole-mount skeletal staining at the rib bones in palovarotene and vehicle treated Fsp1-Ext1$^{CKO}$ mice

| No. of Fsp1-Ext1$^{CKO}$ mice | Treatment | Total number of OCs at the rib bones Mean (95% CI) |
|---|---|---|
| 9 | Palovarotene (1.05 mg/kg daily × 28 days) | 28.33 (23.23-33.43) |
| 3 | Vehicle (daily × 28 days) | 147.3 (99.27-195.4) |

TABLE 2

Mean occurrence of the response (number of rib bones showing no OC vs. number of rib bones showing at least one OC) in palovarotene and vehicle treated Fsp1-Ext1$^{CKO}$ mice

| | Outcome | |
|---|---|---|
| Treatment | Number of rib bones showing at least one OC | Number of rib bones showing no OC |
| Palovarotene (1.05 mg/kg daily × 28 days) | 16 | 8 |
| Vehicle (daily × 28 days) | 24 | 0 |

Example 2—Effects of Palovarotene on Crown-Rump Length in a MO Mouse Model

Figure 3:
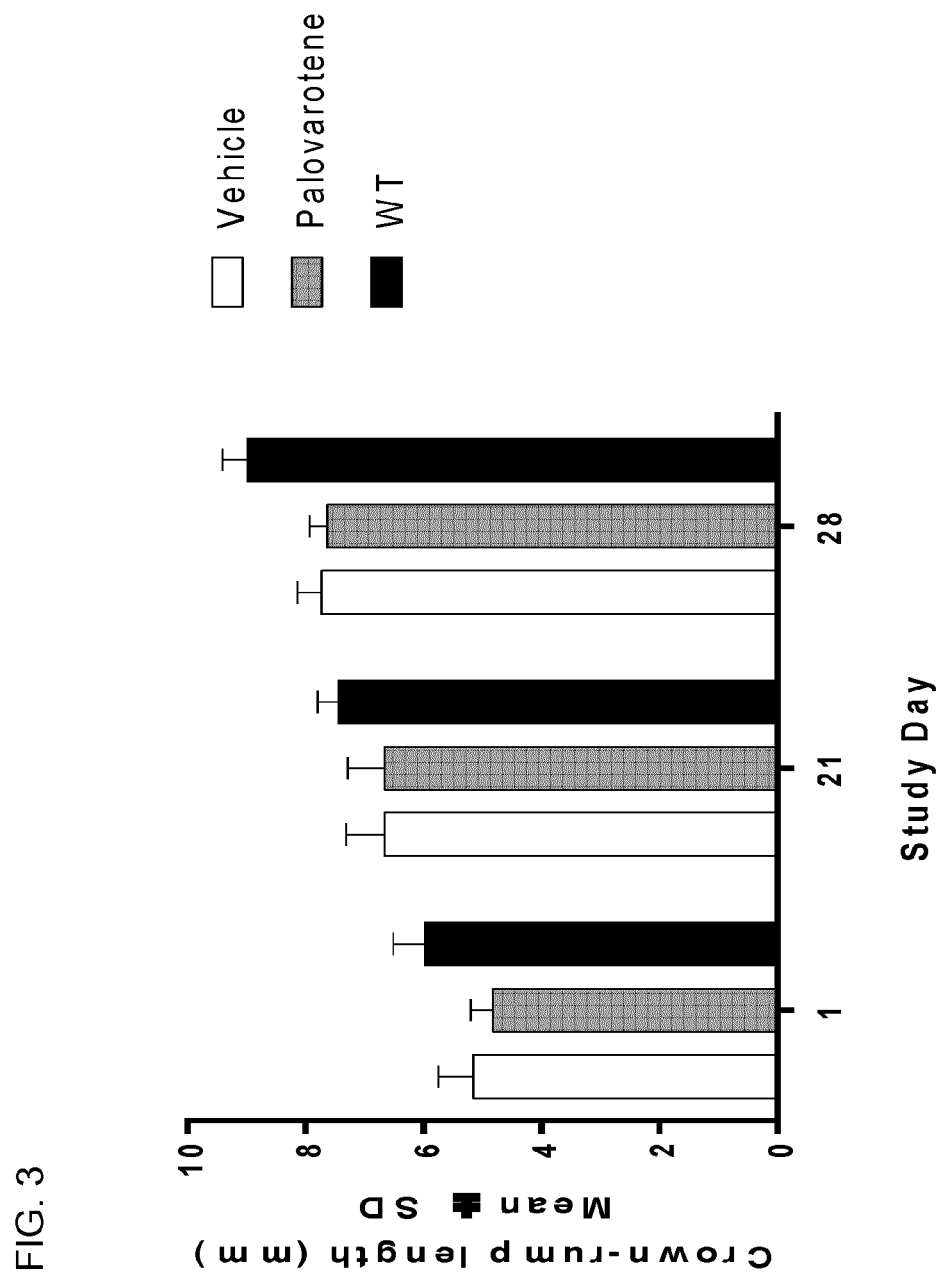
FIG. 3 a graph showing the effect of palovarotene treatment on crown-rump length in Fsp1-Ext1$^{CKO}$ mice.

Crown-rump length, defined as mouse body length from snout to base of the tail, was measured using a ruler in vehicle and palovarotene treated Fsp1-Ext1CKO mice and untreated wild-type (WT) littermates at baseline (Study Day 1) and, 3 and 4 weeks post initiation of palovarotene treatment (Study Day 21 and 28, respectively). As show in FIG. 3, palovarotene treatment had no effect on crown-rump length after 4 weeks of daily oral treatment in Fsp1-Ext1CKO mice compared to vehicle controls.

In summary, as shown by the Examples, palovarotene treatment was able to maintain long bone growth, and did not interfere with normal bone growth in the animal. Furthermore, palovarotene treatment reduced the number and size of osteochondromas observed. We also observed that the animals exhibited reduced cartilage hyperplasia.

Example 3—Dose Response of Palovarotene to Inhibit OC Formation in Fsp1-Ext1$^{cko}$ Mice Nonclinical pharmacology data: Fsp1-Ext1CKO mice were administered three doses of palovarotene (0.269 mg/kg [low], 0.882 mg/kg [mid], or 1.764 mg/kg [high]) for 28 consecutive days starting treatment at Day 14 postpartum (P14 cohort), or for 21 consecutive days starting at Day 21 postpartum (P21 cohort). Palovarotene inhibited the occurrence of OCs in a dose-dependent manner compared to vehicle controls. Greater efficacy was observed with earlier and longer dosing in the P14 cohort compared to the P21 cohort.

To determine the dose exposure response, exposure in this study was extrapolated based on pharmacokinetic data obtained from adult wild-type (WT) mice with the assumption that pharmacokinetics in adult WT mice are similar to juvenile Fsp1-Ext 1CKO mice.

PVO was efficacious in a mouse model at corresponding exposure levels; exposure at EC50 for % decreases in OCs at rib bones ranged from 57 ng·hr/mL to 173 ng·hr/mL in juvenile Fsp1-Ext 1cko mice.

Figure 4:
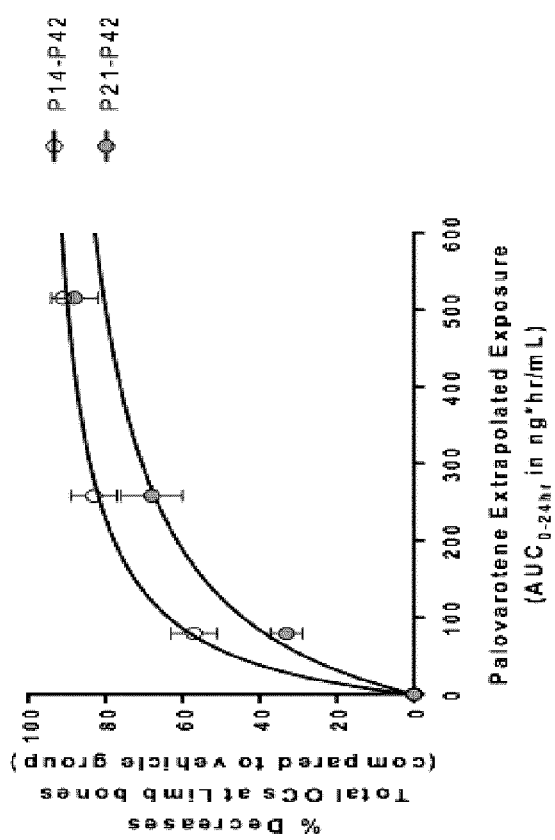
FIG. 4 is a series of graphs showing the dose-response of palovarotene treatment on the occurrence of OCs in rib bones (left) and limb bones (right) in Fsp1-Ext1$^{CKO}$ mice.
Figure 4:
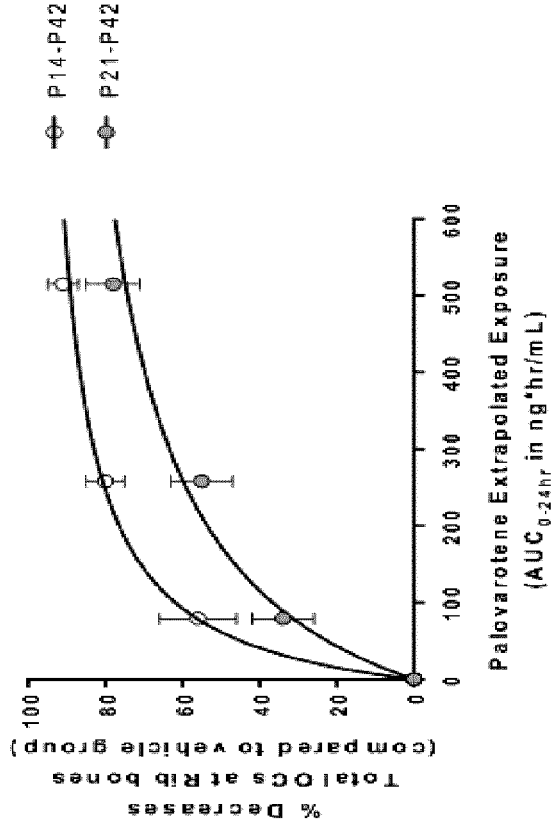

Data (the percent decrease in total OCs at rib and limb bones) are presented as a function of the extrapolated exposure in FIG. 4. The EC50 at $AUC_{0-24\,hr}$ identified for the P14 cohort was 57-62 ng·hr/mL and for the P21 cohort was 125-173 ng·hr/mL).

Example 4—Effects of Palovarotene on Crown-Rump Length in a MO Mouse Model

Pharmacokinetic modeling was performed to determine the appropriate weight-adjusted doses for pediatric subjects that would provide similar exposure to adults receiving either 2.5 or 5.0 mg palovarotene. The AUC and $C_{max}$ predictions for body weight are summarized in Table 3.

TABLE 3

Weight-Adjusted Dosage Groups based on Projected Pharmacokinetic Parameters

| | 10 to <20 kg | | >20 to 40 kg | | >40 to 60 kg | | ≥60 to 80 kg | |
|---|---|---|---|---|---|---|---|---|
| | 2.5 mg | 1.0 mg | 3.0 mg | 1.5 mg | 4.0 mg | 2.0 mg | 5.0 mg | 2.5 mg |
| $AUC_{0-24\,h}$ (h · ng/mL) | 211-227 | 85-91 | 214-252 | 107-126 | 235-285 | 118-143 | 231-294 | 115-147 |
| $C_{max}$ (ng/mL) | 34-37 | 14-15 | 36-41 | 18-21 | 40-48 | 20-24 | 40-50 | 20-25 |

The results show that the weight based dosing regimen yielded exposures across the different weight categories ranging from 85 to 147 ng·hr/mL for the 2.5 mg equivalent doses and from 211 to 294 ng·hr/mL for the 5.0 mg equivalent doses. Of note, the predicted exposures for the weight adjusted doses in the lower weight categories are slightly lower to provide a margin of safety.

Table 4 summarizes the pharmacokinetic parameters of mean and median $AUC_{0-24}$ values for subjects receiving 2.5 mg and 5.0 mg equivalent doses of palovarotene. Skeletally mature subjects received fixed dose regimens, while the skeletally immature subjects <18 years old were dosed via weight adjusted equivalent doses. The observed exposures using weight based dosing tended to be lower than fixed dosing, however the number of subjects providing samples in the 2.5 mg group is very low. These results will be updated as more data become available.

TABLE 4

Observed Pharmacokinetic Parameters in Pediatric Population in Weight-Based Dosing Regimen

|  | PVO 2.5 mg | | PVO 5 mg | |
| --- | --- | --- | --- | --- |
|  | Fixed Dose | Weight-Adjusted Equivalent | Fixed Dose | Weight-Adjusted Equivalent |
| Overall, N | 4 | 3 | 15 | 6 |
| $AUC_{0-24\ h}$, ng · h/mL | | | | |
| Mean (SD) | 176 (85) | 98 (73) | 347 (144) | 249 (88) |
| Median | 149 | 78 | 320 | 218 |
| Min, max | 107, 31 | 37, 179 | 144, 667 | 139, 363 |
| AUC Ratio (A/P) | | | | |
| Mean (SD) | 1.1 (0.7) | 0.8 (0.6) | 1.3 (0.7) | 1.0 (0.3) |
| Median | 0.9 | 0.6 | 1.1 | 0.9 |
| Min, max | 06, 21 | 0.3, 1.4 | 0.6, 2.9 | 0.5, 1.4 |

One other parameter known to impact systemic exposure of palovarotene is food. For the clinical studies, all subjects are instructed to administer study medication at approximately the same time each day, and following a full meal, although the exact amount consumed is not recorded. Overall, the observed exposures are in good agreement with predicted exposures as demonstrated by the AUCA/P ratio of ~1, indicating that the dosing regimen achieved the expected exposures.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

What is claimed is:

1. A method of treating a subject with multiple osteochondroma (MO), comprising administering to the subject an effective amount of palovarotene ((E)-4-(2-{3-[(1H-pyrazole-1-yl)methyl]-5,5,8,8 tetramethyl-5,6,7,8-tetrahydronaphthalene-2-yl}vinyl)benzoic acid), or a pharmaceutically acceptable salt thereof.

2. The method of claim 1, wherein the method comprises reducing in size an osteochondroma in the subject with MO.

3. The method of claim 2, wherein the method reduces in average size osteochondromas in the subject.

4. The method of claim 1, wherein the method comprises slowing growth of an osteochondroma in the subject with MO.

5. The method of claim 1, wherein the osteochondroma is formed:
    (a) adjacent to an area of bone growth;
    (b) adjacent to a growth plate;
    (c) on a perichondrium;
    (d) on an epiphysis of a bone;
    (e) on a long bone;
    (f) on a flat bone;
    (g) on a hip bone, a shoulder blade, a rib, a femur, a tibia, a humerus, a fibula, a pelvic bone, or a vertebra;
    (h) on a surface of a bone; and/or
    (i) in a diaphysis of a bone.

6. The method of claim 5, wherein the osteochondroma is formed:
    (a) on a groove of Ranvier of the perichondrium; or
    (b) at an end of the long bone.

7. The method of claim 1, wherein the method:
    (a) reduces in number osteochondromas in the subject;
    (b) reduces in number bones that have at least one osteochondroma in the subject;
    (c) does not cause any damage to a growth plate of the subject while the subject is treated;
    (d) does not interfere with normal bone growth of the subject;
    (e) reduces bone morphogenic protein (BMP) level and/or BMP signaling in a perichondrium of the subject;
    (f) reduces BMP level and/or BMP signaling in an epiphysis of a bone of the subject; and/or
    (g) reduces BMP level and/or BMP signaling in an overgrown cartilage of the subject.

8. The method of claim 7, wherein the method reduces BMP level and/or BMP signaling in a groove of Ranvier of the perichondrium of the subject.

9. The method of claim 1, where the method comprises reducing cartilage hyperplasia in the subject with MO.

10. The method of claim 1, wherein the subject does not have an osteochondroma.

11. The method of claim 1, wherein the amount of palovarotene administered to the subject is between 0.5 and 9 mg daily.

12. The method of claim 11, wherein the subject weighs from 5 to 20 kg.

13. The method of claim 1, wherein the amount of palovarotene administered to the subject is between 0.5 and 12 mg daily.

14. The method of claim 13, wherein the subject weighs from 20 to 40 kg.

15. The method of claim 1, wherein the amount of palovarotene administered to the subject is between 0.5 and 15 mg daily.

16. The method of claim 15, wherein the subject weighs from 40 to 60 kg.

17. The method of claim 1, wherein the amount of palovarotene administered to the subject is between 0.5 and 20 mg daily.

18. The method of claim 17, wherein the subject weighs more than 60 kg.

19. The method of claim 1, wherein the subject
    (a) is a child or an adolescent who is not fully grown; and/or
    (b) has a mutant exostosin gene.

20. The method of claim 19, wherein:
(a) the child or adolescent has not achieved full skeletal maturity; or
(b) the mutant exostosin gene is a mutant Ext1, Ext2, or Ext3 gene.

21. The method of claim 1, wherein long bone growth of the subject is maintained while the subject is treated.

22. The method of claim 1, wherein
(a) the subject weighs from 5 to 20 kg and the amount of palovarotene administered to the subject is between 1.0±0.5 and 3.0±0.5 mg daily;
(b) the subject weighs from 10 to 20 kg and the amount of palovarotene administered to the subject is between 1.0±0.5 and 3.0±0.5 mg daily;
(c) the subject weighs from 10 to 20 kg and the amount of palovarotene administered to the subject is 1.0±0.1 mg daily;
(d) the subject weighs from 10 to 20 kg and the amount of palovarotene administered to the subject is 2.5±0.25 mg daily;
(e) the subject weighs from 20 to 40 kg and the amount of palovarotene administered to the subject is between 1.0±0.5 and 4.0±0.5 mg daily;
(f) the subject weighs from 20 to 40 kg and the amount of palovarotene administered to the subject is 1.5±0.15 mg daily;
(g) the subject weighs from 20 to 40 kg and the amount of palovarotene administered to the subject is 3.0±0.3 mg daily;
(h) the subject weighs from 40 to 60 kg and the amount of palovarotene administered to the subject is between 2.0±0.5 and 5.0±0.5 mg daily;
(i) the subject weighs from 40 to 60 kg and the amount of palovarotene administered to the subject is 2.0±0.2 mg daily;
(j) the subject weighs from 40 to 60 kg and the amount of palovarotene administered to the subject is 4.0±0.4 mg daily;
(k) the subject weighs more than 60 kg and the amount of palovarotene administered to the subject is between 2.0±0.5 and 6.0±0.5 mg daily;
(l) the subject weighs more than 60 kg and the amount of palovarotene administered to the subject is 2.5±0.25 mg daily; or
(m) the subject weighs more than 60 kg and the amount of palovarotene administered to the subject is 5.0±0.5 mg daily.

23. The method of claim 1, wherein the method comprises inhibiting formation of an osteochondroma in the subject with MO.

\* \* \* \* \*